US009850279B2

(12) United States Patent
Donini et al.

(10) Patent No.: US 9,850,279 B2
(45) Date of Patent: Dec. 26, 2017

(54) PEPTIDES AND ANALOGS FOR USE IN THE TREATMENT OF ORAL MUCOSITIS

(71) Applicant: Soligenix, Inc., Princeton, NJ (US)

(72) Inventors: Oreola Donini, Coquitlam (CA); Annett Rozek, Port Moody (CA); Jackson Lee, Richmond (CA); John North, Comox (CA); Michael Abrams, Custer, WA (US)

(73) Assignee: Soligenix, Inc., Princeton, NJ (US)

( * ) Notice: Subject to any disclaimer, the term of this patent is extended or adjusted under 35 U.S.C. 154(b) by 0 days.

(21) Appl. No.: 15/021,889

(22) PCT Filed: Aug. 11, 2014

(86) PCT No.: PCT/US2014/050516
§ 371 (c)(1),
(2) Date: Mar. 14, 2016

(87) PCT Pub. No.: WO2015/038264
PCT Pub. Date: Mar. 19, 2015

(65) Prior Publication Data
US 2016/0229890 A1 Aug. 11, 2016

Related U.S. Application Data

(60) Provisional application No. 61/877,767, filed on Sep. 13, 2013.

(51) Int. Cl.
| | |
|---|---|
| *A61K 38/00* | (2006.01) |
| *C07K 7/06* | (2006.01) |
| *C07K 5/11* | (2006.01) |
| *A61K 31/573* | (2006.01) |
| *A61K 38/08* | (2006.01) |
| *A61K 45/06* | (2006.01) |

(52) U.S. Cl.
CPC .............. *C07K 7/06* (2013.01); *A61K 31/573* (2013.01); *A61K 38/08* (2013.01); *A61K 45/06* (2013.01); *C07K 5/1019* (2013.01)

(58) Field of Classification Search
None
See application file for complete search history.

(56) References Cited

U.S. PATENT DOCUMENTS

| | | |
|---|---|---|
| 7,629,438 B2 | 12/2009 | Huang et al. |
| 8,519,096 B2 | 8/2013 | Ling et al. |
| 2010/0183749 A1 | 7/2010 | Brey |
| 2013/0224231 A1 | 8/2013 | Donini et al. |

FOREIGN PATENT DOCUMENTS

WO 2008143679 11/2008

OTHER PUBLICATIONS

Redding. Cancer Therapy-Related Oral Mucositis. (2005) Journal of Dental Education 69(8):919-929.
Donnelly et al. Antimicrobial therapy to prevent or treat oral mucositis. (2003) The Lancet 3: 405-12.
Lalla et al. MASCC/ISOO Clinical Practice Guidelines for the Management of Mucositis Secondary to Cancer Therapy. (2014) Cancer 1453-1461.

*Primary Examiner* — Jeanette Lieb
(74) *Attorney, Agent, or Firm* — Lewis Kohn & Walker LLP; David M. Kohn; Kari Moyer-Henry

(57) ABSTRACT

Preclinical data obtained in models of chemotherapy-induced mucositis, radiation-induced mucositis, neutropenic infection and colitis indicate oral mucositis is a promising indication for Innate Defense Regulator (IDR) peptides. Preclinical efficacy results obtained with IDRs in mouse and hamster models of mucositis indicate that dosing every third day should be able to cover the mucositis "window" with seven to fourteen doses, depending on the duration of chemotherapy or radiation exposure. IDRs have also shown efficacy in mouse models of chemotherapy-induced oral and gastrointestinal mucositis, consistent with the response of the innate immune response to chemotherapy and/or radiation damage. IDRs are also effective at reducing bacterial burden and improve survival in the presence or absence of antibiotic treatment in various murine infection models.

6 Claims, 13 Drawing Sheets

* Absence of a bar in panels A indicates that all mice died (0% survival).

* Absence of a bar in panels C and D indicates that all mice had a zero score, yielding a mean and standard error of the mean (SEM) of 0 ± 0.

PEPTIDES AND ANALOGS FOR USE IN THE TREATMENT OF ORAL MUCOSITIS

RELATED APPLICATIONS

This application is a United States National Stage Application claiming priority under 35 U.S.C. 371 from International Patent Application No. PCT/US14/50516 filed on Aug. 11, 2014, which claims the benefit of priority from U.S. Provisional Application No. 61/877,767, filed on Sep. 13, 2013, the entire contents of which are herein incorporated by reference.

INTRODUCTION

Innate Immune System

The innate immune response is an evolutionarily conserved protective system associated with the barriers between tissues and the external environment, such as the skin, the orogastric mucosa and the airways. Providing rapid recognition and eradication of invading pathogens as well as a response to cellular damage, it is often associated with inflammatory responses and is a key contributor to the activation of adaptive immunity. Innate defenses are triggered by the binding of pathogen and/or damage associated molecules (PAMPs or DAMPs) to pattern-recognition receptors, including Toll-like receptors (TLRs). Pattern recognition receptors are found in and on many cell types, distributed throughout the body in both circulating and tissue resident compartments, and serve to provide early "danger" signals that lead to the release of non-specific antimicrobial molecules, cytokines, chemokines, and host defense proteins and peptides as well as the recruitment of immune cells (neutrophils, macrophages, monocytes) in a highly orchestrated fashion (Janeway 2002; Beutler 2003; Beutler 2004; Athman 2004; Tosi 2005; Doyle 2006; Foster 2007; Matzinger 2002). Moreover the innate immune system is directly involved in the generation of tolerance to commensal microbiota in the gastrointestinal tract and in gastrointestinal repair and immune defense (Santaolalla, 2011; Molloy 2012).

Mucositis

Mucositis is the clinical term for damage done to the mucosa by anticancer therapies. It can occur in any mucosal region, but is most commonly associated with the mouth, followed by the small intestine. Though many mucositis scales are used clinically, the two most commonly used grading systems are the NCI and WHO scales.

The mechanisms of mucositis have been extensively studied and have been recently linked to the interaction of chemotherapy and/or radiation therapy with the innate defense system (Sonis 2010). Bacterial infection of the ulcerative lesions is now regarded as a secondary consequence of dysregulated local inflammation triggered by therapy-induced cell death, rather than as the primary cause of the lesions. Mucositis affects 500,000 people in the US per year and occurs in 40% of patients receiving chemotherapy (Sonis 2010, Curr. Op.). Mucositis almost always occurs in patients with head and neck cancer treated with radiation therapy (>80% incidence of severe mucositis) (Elting et al. 2008). Mucositis is common (40-100% incidence) in patients undergoing high dose chemotherapy and stem cell transplantation (SCT) where the incidence and severity of mucositis depends greatly on the nature of the conditioning regimen used for myeloablation (Murphy 2007). Of well-established chemotherapy drugs, 5-FU and irinotecan are particularly noted for causing mucositis but it also occurs with newer agents such as mTOR inhibitors and kinase inhibitors (Mateus et al. 2009; Sankhala et al. 2009). Mucositis can be seriously debilitating and can lead to infection, sepsis, the need for parenteral nutrition and narcotic analgesia. The intestinal damage causes severe diarrhea. These symptoms can limit the doses and duration of cancer treatment, thus leading to sub-optimal treatment outcomes including reduced survival. Direct and indirect consequences of mucositis have been estimated to add ~$18K per patient to cancer treatment costs (Nonzee et al. 2008). Mucositis occurs 3-12 weeks after the initiation of radiation, or 3-12 days after the initiation of chemotherapy, and resolves after 2-3 weeks, assuming no further chemotherapy or radiation treatment is undertaken.

RIVPA (SEQ ID NO. 5) is an IDR (Innate Defense Regulator), a new class of short, synthetic peptides with a novel mechanism. Designed to mimic one of the recently discovered functions of natural mucosal defense peptides, IDRs have no direct antibiotic activity but modulate host responses, increasing survival after infections with a broad range of bacterial Gram-negative and Gram-positive pathogens, as well as accelerating resolution of tissue damage following exposure to a variety of agents including bacterial pathogens, trauma and chemo- or radiation-therapy.

Based on preclinical data obtained in models of chemotherapy-induced mucositis, radiation-induced mucositis, neutropenic infection and colitis, oral mucositis is a promising indication for RIVPA (SEQ ID NO. 5) and other IDR peptides. Since the drug would be given soon after the chemotherapy infusion or radiation, the IV dosage form of RIVPA (SEQ ID NO. 5) is well suited to the mucositis indication. Preclinical efficacy results obtained with RIVPA (SEQ ID NO. 5) in mouse and hamster models of mucositis indicate that dosing every third day should be able to cover the mucositis "window" with seven to fourteen doses, depending on the duration of chemotherapy or radiation exposure.

With regard to breast cancer, ~20% of patients receiving ACT therapy suffer ulcerative mucositis during their first round of chemotherapy but ~70% of that subset of patients will have ulcerative mucositis on their second round (Sonis 2010). This represents a "high risk" patient population that would benefit from RIVPA (SEQ ID NO. 5) treatment. There are currently no systemic agents approved for the amelioration of mucositis in this population.

Patients undergoing high dose chemotherapy and SCT for the treatment of hematologic cancers are an immunosuppressed population at high risk of infection. In this treatment, high doses of chemotherapy (sometimes in combination with radiation), a "conditioning regimen", are used to kill a large proportion of the cancer cells. These treatment levels would cause lethal myelosuppression unless stem cells (from bone marrow or blood) are administered afterwards to allow reconstitution of blood cells. Autologous transplants use the patient's own stem cells for this purpose while allogeneic transplants use cells from a matched healthy donor. Autologous transplants are used most often in the treatment of Multiple Myeloma (MM) and non-Hodgkins Lymphoma (NHL). Allogeneic transplants are typically used to treat leukemias such as AML.

With regard to SCT, until recently the various conditioning chemotherapy regimens all resulted in a relatively high rate of oral mucositis (40-100%) and in most US centers these patients are managed in-hospital. Oral mucositis associated with radiation and/or chemoradiation therapy for head & neck cancer is a major problem, with 85% of subjects suffering some degree of mucositis—42% being grade 3 or 4.

Acute Radiation Syndrome

Acute radiation syndrome (ARS) is a serious illness that occurs when the entire body (or most of it) receives a high dose of radiation, typically over a short period of time. Many survivors of the Hiroshima and Nagasaki atomic bombs in the 1940s and many of the firefighters who first responded after the Chernobyl Nuclear Power Plant accident in 1986 became ill with ARS (CDC 2013).

Individuals exposed to radiation will get ARS only if the:
 the radiation dose was high (doses from medical procedures such as chest X-rays are too low to cause ARS),
 the radiation was penetrating (that is, able to reach internal organs),
 the person's entire body, or most of it, received the dose, and
 the radiation was received in a short time, usually within minutes.

Radiation induces dose-proportional injury to mammalian cells and tissues. At low doses, the injury may be limited to point mutations in somatic and/or germ-line DNA that may be associated with long-term effects such as an increased risk of cancer or birth defects. At intermediate doses, radiation induces chromosomal abnormalities such as breaks and translocations, which again increases the risk of cancers and birth defects, and if severe enough will result in the death of rapidly dividing cells within hours of exposure. At very high doses, radiation can denature proteins, resulting in almost immediate death of cells and tissues. The tissues with rapidly dividing cells that are the most commonly affected by moderate doses of radiation include the bone marrow, the gastrointestinal tract and the testis. Exposure to radiation is associated with acute effects, including skin rashes and burns, bone marrow failure, including anemia, depressed white blood cell counts, and thrombocytopenia, as well as gastrointestinal toxicity such as diarrhea, and more chronic effects such as the development of tumors, especially sarcomas and leukemias, and birth defects.

The first symptoms of ARS typically are nausea, vomiting, and diarrhea. These symptoms will start within minutes to days after the exposure, will last for minutes up to several days, and may come and go. Then the person usually looks and feels healthy for a short time, after which he or she will become sick again with loss of appetite, fatigue, fever, nausea, vomiting, diarrhea, and possibly even seizures and coma. This seriously ill stage may last from a few hours up to several months.

People with ARS typically also have some skin damage. This damage can start to show within a few hours after exposure and can include swelling, itching, redness of the skin and hair loss. As with the other symptoms, the skin may heal for a short time, followed by the return of swelling, itching, and redness days or weeks later. Complete healing of the skin may take from several weeks up to a few years depending on the radiation dose the person's skin received.

The gastrointestinal manifestation of ARS is referred to as gastrointestinal acute radiation syndrome or GI-ARS. GI-ARS consists of diarrhea, dehydration, enterobacterial infection, and in severe cases, septic shock and death (Potten 1990). Following radiation exposure, GI-ARS is thought to be caused by direct damage to stem cells within the base of the crypts of Ueberkuhn, resulting in mitotic cessation and death through apoptotic mechanisms (Potten 1997a, Potten 1997b). The integrity of gastrointestinal mucosa depends on a rapid proliferation of a pool of pluripotent stem cells at the bottom of the crypts (Brittan 2002, Gordon 1994, Potten 1997b). Thus, stem cell death is thought to be the critical element in this process, since surviving intestinal stem cells appear to be sufficient for reconstitution of a crypt-villus unit (Potten 1990). Renewal of the intestinal epithelial barrier depends upon an active stem cell compartment similar to the hematopoietic system. Intestinal crypt-villus precursor clonogen cells are particularly sensitive to ionizing radiation exposure such that with increasing radiation dose, crypt-villus clonogen cells cannot produce enough cells to repopulate the villi. This results in blunting and diminution in villus height and eventual functional incapacity, leading to decreased nutrient absorption and barrier function, loss of fluid and electrolytes, and bacterial translocation through the intestinal barrier (Monti 2005, Zhao 2009). Above 8 Gray (Gy), dose-dependent stem cell death leads to reduction of crypt regeneration, until the level of regeneration is insufficient to rescue the GI mucosa. From studies in mice, progressive denudation of the epithelium leads, by day 6 to 7 after radiation, to death from the GI syndrome. When mitotic activity resumes, precipitous depletion of crypts ensues, presumably as a result of the onset of reproductive death of crypt clonogens (Withers 1971). At the lower-dose range (8-13 Gy), surviving clonogens regenerate the crypt system, leading to complete recovery of injured mucosa. At doses exceeding 14 Gy, massive clonogen loss causes collapse of the crypt-villus system, mucosal denudation and animal death from the gastrointestinal syndrome (Paris 2001; Potten 1990; Withers 1971; Withers 1969).

The intestinal stem cell compartment is not the only compartment sensitive to ionizing radiation. Another critical factor involving the response of the GI tract to a major physical insult is hypoperfusion of the intestine. Persistent gut hypoperfusion is an important inciting event in the development of the systemic inflammatory response syndrome and multi-organ failure (MOF) (Moore 1999). Increased intestinal vascular permeability together with capillary leakage has been observed in the early period after irradiation (Cockerham 1984; Eddy 1968, Willoughby 1960). Additional post-irradiation alterations include moderate dilatation and tortuosity of small arterial vessels, reduction in numbers and/or lengths of vessels followed by later occurring hemorrhagic patterns (Eddy 1968). There has been an ongoing controversy concerning whether the primary lesion after irradiation is intestinal epithelium stem cell death or a result of endothelial cell death (Kirsch 2010). Regardless of primary lesion, it is clear that irradiation results in a complex injury response including death of intestinal epithelial cells, endothelial cells and gut hypoperfusion (Williams 2010).

Treatment modalities such as hematopoletic growth factors, i.e., granulocyte- and/or granulocyte-macrophage colony stimulation factors (G-CSF and G/M-CSF) and erythropoietin (EPO), and hematopoietic stem cell/bone marrow transplantation, are available to attenuate mortality from hematopoletic failure.

The chance of survival for people with ARS decreases with increasing radiation dose. The cause of death within 15 days of radiation exposure is usually damage to the GI tract whereas after 15 days death usually is a consequence of bone marrow injury. For the survivors, the recovery process may last from several weeks up to 2 years (CDC 2013).

There is an urgent need for the development of radiation mitigators, as there currently are none approved for the treatment of acute radiation syndrome. RIVPA (SEQ ID NO.

5) has the potential to decrease the acute mortality in ARS, enabling supportive care efforts, and to aid in the recovery of skin damage.

Infection

A variety of microorganisms, including viruses, bacteria, fungi and parasites can cause disease. Microbial cells are distinct from cells of animals and plants that are unable to live alone in nature, existing only as parts of multicellular organisms. Microbial cells can be pathogenic or non-pathogenic, depending, in part, on the microorganism and the status of the host. For example, in an immunocompromised host, a normally harmless bacterium can become a pathogen. Entry into host cells is critical for the survival of bacterial pathogens that replicate in an intracellular milieu. For organisms that replicate at extracellular sites, significance of bacterial entry into host cells is less well defined.

Drug resistance remains an obstacle in the ongoing effort to fight infection. For example, penicillin was effective in treating Stophylococcus aureus until the bacterium became resistant. Throughout the second half of the 20$^{th}$ century, new antibiotics, such as vancomycin and methicillin, were developed; these successfully cured S. aureus infection. However, methicillin-resistant strain of S. aureus evolved in the 1970s, and have been plaguing hospitals worldwide ever since. More recently, vancomycin-resistant strains of S. aureus have surfaced.

With the increasing threat of resistance to antimicrobial drugs and the emergence of new infectious diseases, there exists a continuing need for novel therapeutic compounds. Therapeutics that act on the host, not the pathogen, are desirable, because they do not encourage pathogenic resistance. In particular, drugs that act on the host via the innate immune system provide a promising source of therapeutics. There is evidence to indicate that innate responses are instrumental in controlling most infections, and also contribute to inflammatory responses. Inflammatory responses triggered by infection are known to be central components of disease pathogenesis. An ability to increase host resistance to infection, while controlling inflammation, would be very beneficial in the ongoing battle against infection, including infection caused by resistant organisms.

IDRs and the Innate Immune System

Innate Defense Regulators (IDRs) interact with intracellular signaling events and modulate the innate defense response. Whereas much of the initial work with the IDRs focused on their role in fighting infection while controlling inflammation, recent results in animal models of chemotherapy- or radiation-induced mucositis and wound healing suggest that IDRs can be beneficial during the responses to a broader range of damage-inducing agents beyond pathogens. IDRs treat and prevent infections by selectively modifying the body's innate defense responses when they are activated by PAMPs or DAMPs, without triggering associated inflammation responses (Matzinger 2002). The same mechanisms underlie positive effects seen in mucositis and wound healing models, where signaling downstream of the recognition of DAMPs is affected. RIVPA (SEQ ID NO. 5) has demonstrated safety in humans and efficacy in animal models of fractionated radiation-induced and chemotherapy-induced oral mucositis, in models of chemotherapy induced damage to the gastro-intestinal tract and in models of local and systemic Gram-positive and Gram-negative Infection in immunocompetent and immunocompromised hosts.

DETAILED DESCRIPTION OF THE INVENTION

Figure 1:
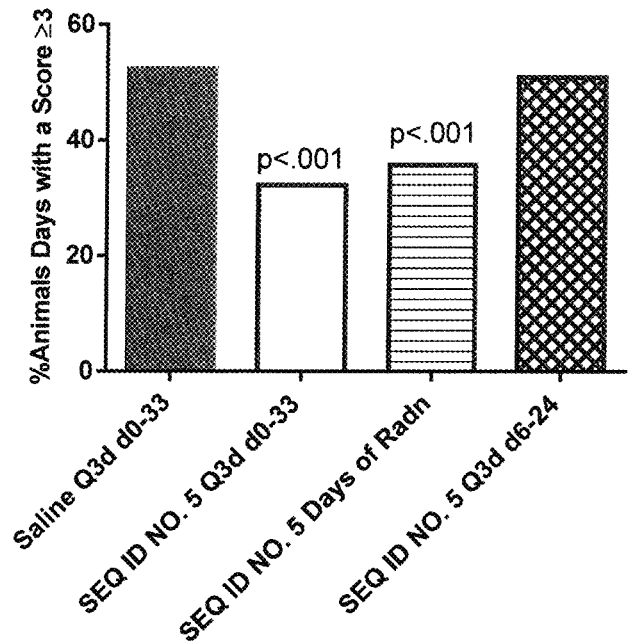
FIG. 1. RIVPA (SEQ ID NO. 5) reduces the duration of severe oral mucositis in a fractionated radiation model.

It is an object of the present invention to provide an isolated peptide consisting of the amino acid sequence of R(tBg)V1KR(tBg)V2, wherein tBg=tert-butyl glycine and further wherein R(tBg)V2 is linked via an amide bond between V1 and K.

It is an object of the present invention to provide An isolated peptide consisting of the amino acid sequence of RIV(mp2)A-NH2, wherein mp2=4-Amino-1-methyl-1H-pyrrole-2-carboxylic acid

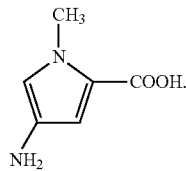

It is yet another object of the present invention to provide a method of treating oral mucositis in a subject who has been exposed to a damaging amount of radiation or chemotherapeutic agents, comprising administering to the patient an effective amount of:
 a) a peptide comprising an amino acid sequence of Table 1; or
 b) a peptide comprising the amino acid sequence of any of SEQ ID NOs: 5, 7, 10, 14, 17, 18, 22, 23, 24, 27, 28, 31, 34, 35, 63, 64, 66-69, 72, 76, 77, 90, 91 and 92 or a pharmaceutical salt, ester or amide thereof and a pharmaceutically-acceptable carrier, diluent or excipient.

It is an object of the present invention to provide a method of treating oral mucositis in a subject who has been exposed to a damaging amount of radiation or chemotherapeutic agents, comprising administering to the patient an effective amount of:
 a) a peptide comprising an amino acid sequence of up to 7 amino acids, said peptide comprising the amino acid sequence of $X_1X_2X_3P$ (SEQ ID NO: 56), wherein:
  X1 is R;
  X2 is I or V, wherein X2 can be N-methylated;
  X3 is I or V, wherein X3 can be N-methylated;
  P is proline or a proline analogue;
  wherein SEQ ID NO: 56 if the first four amino acids at the N-terminus of the peptide, or a pharmaceutical salt, ester or amide thereof and a pharmaceutically-acceptable carrier, diluent, or excipient; or
 b) a peptide comprising the amino acid sequence of any of SEQ ID NOs: 5, 7, 10, 14, 17, 18, 22, 23, 24, 27, 28, 31, 34, 35, 63, 64, 66-69, 72, 76, 77, 90 and 92 or a pharmaceutical salt, ester or amide thereof and a pharmaceutically-acceptable carrier, diluent or excipient.

It is another object of the present invention to provide a method of treating oral mucositis in a subject who has been exposed to a damaging amount of radiation or chemotherapeutic agents, wherein the peptide is SEQ ID NO: 5 or a pharmaceutical salt, ester, or amide thereof and a pharmaceutically-acceptable carrier, diluent, or excipient.

It is another object of the present invention to provide a method of treating oral mucositis in a subject who has been exposed to a damaging amount of radiation or chemotherapeutic agents, wherein the peptide is administered orally, parenterally, transdermally, intranasally.

It is yet another object of the present invention to provide a method of treating oral mucositis in a subject who has been exposed to a damaging amount of radiation or chemotherapeutic agents, wherein the effective amount of peptide administered to a subject is at least 1 mg/kg. In a preferred embodiment the effect amount of peptide administered to a subject is about 1.5 mg/kg to 6 mg/kg.

It is yet another object of the present invention to provide a method of treating oral mucositis in a subject who has been exposed to a damaging amount of radiation or chemotherapeutic agents, wherein the peptide is administered to the subject every third day during radiation or chemotherapeutic agent administration.

It is still another object of the present invention to provide a method of treating oral mucositis in a subject who has been exposed to a damaging amount of radiation or chemotherapeutic agents, wherein the peptide is administered in combination with an oral dosage form of a topically active corticosteroid or a metabolite thereof to the subject, wherein the oral dosage form is effective for topical or local treatment of the gastrointestinal tract and oral cavity of the subject and further wherein the subject exhibits symptoms of inflammation due to tissue damage arising from radiation or chemotherapy treatment. Representative topically active corticosteroids include, but are not limited to, beclomethasone 17,21-dipropionate, aclomethasone dipropionate, budesonide, 22S budesonide, 22R budesonide, beclomethasone-17-monopropionate, clobetasol propionate, diflorasone diacetate, flunisolide, flurandrenolide, fluticasone propionate, halobetasol propionate, halcinodde, mometasone furoate, and triamcinolone acetonide. In a preferred embodiment of this invention, the topically active corticosteroid is beclomethasone dipropionate. The effective amount of topically active corticosteroid in each dosage form may vary from patient to patient, and may be readily determined by one skilled in the art by well-known does-response studies. Such effective amounts will generally range between about 0.1 mg/day to about 8 mg/day, and more typically range from about 2 mg/day to about 4 mg/day.

It is still another object of the present invention to provide a method mitigating the gastrointestinal, hematopoletic and cutaneous impacts of acute radiation syndrome in a subject who has received a high, penetrating dose of radiation to a substantial portion of their body in a short period of time.

It is still another object of the present invention to provide a method of treating acute radiation syndrome in a subject who has received a high, penetrating dose of radiation to a substantial portion of their body in a short period of time, wherein the peptide is administered in combination with an oral dosage form of a topically active corticosteroid or a metabolite thereof to the subject, wherein the oral dosage form is effective for topical or local treatment of the gastrointestinal tract and oral cavity of the subject and further wherein the subject exhibits symptoms of inflammation due to tissue damage arising from radiation or chemotherapy treatment. Representative topically active corticosteroids include, but are not limited to, bedomethasone 17,21-dipropionate, aclomethasone dipropionate, budesonide, 22S budesonide, 22R budesonide, beclomethasone-17-monopropionate, clobetasol propionate, diflorasone diacetate, flunisolide, flurandrenolide, fluticasone propionate, halobetasol propionate, halcinonide, mometasone furoate, and triamcinolone acetonide. In a preferred embodiment of this invention, the topically active corticosteroid is bedomethasone dipropionate. The effective amount of topically active corticosteroid in each dosage form may vary from patient to patient, and may be readily determined by one skilled in the art by well-known does-response studies. Such effective amounts will generally range between about 0.1 mg/day to about 8 mg/day, and more typically range from about 2 mg/day to about 4 mg/day.

It is still another object of the present invention to provide a method of treating and/or preventing Infection (e.g., a microbial infection) in a subject, by administering to the subject a peptide having or comprising the amino acid sequence of TABLE 1 or an analogue, derivative, or variant thereof or obvious chemical equivalent thereof. By way of example, the subject may have, or be at risk of having, infection. In one embodiment, the peptide modulates innate immunity in the subject, thereby treating and/or preventing the infection in the subject.

Exemplary Infections which may be treated and/or prevented by the method of the present invention include an infection by a bacterium (e.g., a Gram-positive or Gram-negative bacterium), an infection by a fungus, an infection by a parasite, and an infection by a virus. In one embodiment of the present invention, the infection is a bacterial Infection (e.g., Infection by *E. coli, Klebsiella pneumoniae, Pseudomonas aeruginosa, Salmonella* spp., *Staphylococcus aureus, Streptococcus* spp., or vancomycin-resistant *enterococcus*). In another embodiment, the infection is a fungal infection (e.g., infection by a mould, a yeast, or a higher fungus). In still another embodiment, the Infection is a parasitic infection (e.g., infection by a single-celled or multicellular parasite, including *Giardia duodenalis, Cryptosporidium parvum, Cyclospora cayetanensis*, and *Toxoplasma gondii*). In yet another embodiment, the infection is a viral infection (e.g., infection by a virus associated with AIDS, avian flu, chickenpox, cold sores, common cold, gastroenteritis, glandular fever, influenza, measles, mumps, pharyngitis, pneumonia, rubella, SARS, and lower or upper respiratory tract infection (e.g., respiratory syncytial virus)).

Formulation of the Dosage Form

The dosage form of RIVPA (SEQ ID NO. 5) is an aqueous, aseptically processed, sterile solution for injection. Each vial contains 5 mL of a 60 mg/mL solution (300 mg of RIVPA (SEQ ID NO. 5)). RIVPA (SEQ ID NO. 5) is formulated in Water for Injection and pH adjusted to a target value of 6.0. The formulation contains no excipients and has an osmolality of ~300 mOsm/kg.

Route of Administration

RIVPA (SEQ ID NO. 5) drug product will be diluted in sterile saline to the appropriate concentration for injection, determined on a mg/kg basis by the recipient's weight and the designated dose level. Diluted RIVPA (SEQ ID NO. 5) will be administered as an intravenous (IV) infusion in 25 mL over 4 minutes, once every third day.

EXAMPLES

Peptide Synthesis

The peptides in Table 1 were synthesized using a solid phase peptide synthesis technique.

All the required Fmoc-protected amino acids were weighed in three-fold molar excess relative to the 1 mmole of peptide desired. The amino acids were then dissolved in Dimethylformaide (DMF) (7.5 ml) to make a 3 mMol solution. The appropriate amount of Rink amide MBHA resin was weighed taking in to account the resin's substitution. The resin was then transferred into the automated synthesizer reaction vessel and was pre-soaked with Dichloromethane (DCM) for 15 minutes.

The resin was de-protected by adding 25% piperidine in DMF (30 ml) to the resin and mixing for 20 minutes. After de-protection of the resin the first coupling was made by mixing the 3 mMol amino acid solution with 4 mMol 2-(1H-benzitriazole-1-yl)-1,1,3,3-tetramethyluronium hexafluorophosphate (HBTU) and 8 mMol N,N-diisopropylethylamine (DIEPA). The solution was allowed to pre-activate for 5 minutes before being added to the resin. The amino acid was allowed to couple for 45 minutes.

After coupling the resin was thoroughly rinsed with DMF and Dimethylacetamide (DMA). The attached Fmoc protected amino acid was deprotected in the same manner described above and the next amino acid was attached using the same coupling scheme AA:HBTU:DIEPA.

After the completion of the synthesis the peptide was cleaved from the resin with the use of a cleavage cocktail containing 97.5% Trifluoroacetic acid (TFA) and 2.5% water. The resin was allowed to swim in the cleavage cocktail for 1½ hours. The solution was then filtered by gravity using a Buchner funnel and the filtrate was collected in a 50 ml centrifugation tube. The peptide was isolated by precipitating with chilled diethyl ether. After centrifuging and decanting diethyl ether the crude peptide was washed with diethyl ether once more before being dried in a vacuum desiccator for 2 hours. The peptide was then dissolved in de-ionized water (10 ml), frozen at $-80°$ C. and lyophilized. The dry peptide was then ready for HPLC purification.

Due to the hydrophilic nature of these peptides the diethyl ether peptide isolation did not work. Therefore a chloroform extraction was required. The TFA was evaporated and the resulting peptide residue was dissolved in 10% acetic acid (15 ml). The Impurities and scavengers were removed from the acetic acid peptide solution by washing the solution twice with chloroform (30 ml). The aqueous peptide solution was then frozen at $-80°$ C. and lyophilized resulting in a powdered peptide ready for HPLC purification.

Peptides +RIxVPA (SEQ ID NO. 33) and +RIVPAx (SEQ ID NO. 34) each contained one N-methyl amino acid. This coupling was carried out by combining the N-methyl amino acid, PyBroP and N-hydroxybenzotriazole*H2O (HOBt) and DIEPA solutions together in the RV containing the resin. After allowing to couple for 45 minutes the N-methyl amino acid was then doubled coupled to ensure complete coupling. It was observed that the coupling following the N-methyl amino acid was not fully complete. Therefore this coupling was performed using N,N,N',N'-Tetramethyl-O-(7-azabenzotriazol-1-yl)uronium hexafluorophosphate (HATU) instead of HBTU. This still resulted in a crude peptide that typically contained two impurities totaling 30-40% of the total purity. The peptide was purified under modified HPLC conditions to isolate the pure peptide peak away from the closely eluting impurities.

R(tBg)V1KR(tBg)V2 (SEQ ID NO. 91) is an 8-residue peptide dendrimer with symmetrical branches occurring off of a fourth amino acid lysine that possesses two functional amine groups. The peptide has been synthesized with solid-phase peptide synthesis techniques, utilizing a di-Fmoc protected fourth amino acid to facilitate the coupling of the branches, using the general synthesis techniques described above.

In addition, these peptides can also be synthesized with solution phase peptide synthesis techniques (Tsuda et al. 2010) and commonly known to experts in the art.

Efficacy in Oral Mucositis

RIVPA (SEQ ID NO. 5) and other IDRs modulate the innate defense response to tissue injury, reducing the severity of damage caused by the inflammatory cascade and enhancing resolution of disease. This attribute of IDRs has been demonstrated in chemotherapy-induced oral and GI mucositis in mice, in radiation-induced oral mucositis in hamsters and in DSS-induced colitis in mice. In each of these models, the Initial damage is thought to trigger a cascade of innate defense signaling which increases the severity of the injury (Marks 2011; Sonis 2010). RIVPA (SEQ ID NO. 5) and other IDRs offset the signaling cascade, reducing the resultant severity of the injury and reducing the duration of severe tissue damage.

The optimum dosing regimen for RIVPA (SEQ ID NO. 5) and other IDRs identified in the MRSA bacteremia model has been further confirmed in injury models, where the longer duration of disease makes repeat dosing more informative. Dosing of 25 mg/kg every third day was found to be optimal, reflecting the durable pharmacodynamic impact of RIVPA and other IDRs (SEQ ID NO. 5) despite its rapid PK clearance (within minutes) from the circulation of mice.

Figure 2:
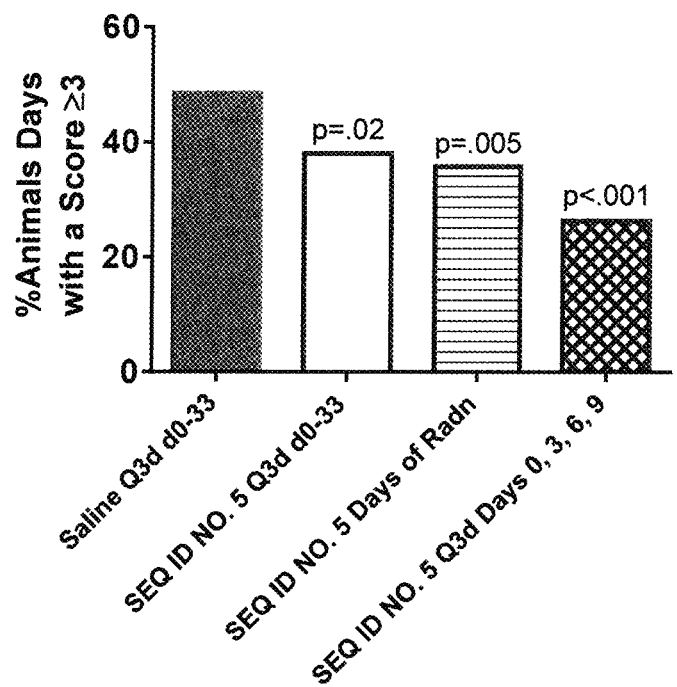
FIG. 2. RIVPA (SEQ ID NO. 5) reduces the duration of severe oral mucositis in a fractionated radiation model using an optimized dosing regimen.

RIVPA (SEQ ID NO. 5) significantly reduced the severity and duration of mucositis in a model of radiation-induced oral mucositis in hamsters, particularly when administered every third day during the fractionated radiation therapy. These studies confirmed that optimal dosing of RIVPA (SEQ ID NO. 5) involves dosing every third day and that the 25 mg/kg dose level is effective. In this model, cannulated male Golden Syrian hamsters were treated with 7.5 Gy of radiation, directed at the everted left cheek pouch, on Days 0, 1, 2, 3, 6, 7, 8 and 9. Mucositis was evaluated every second day between Days 7 and 35, with peak mucositis severity generally occurring around Day 19. In the first study, RIVPA (SEQ ID NO. 5) (25 mg/kg IV) was administered either every third day starting on Day 0 and continuing until Day 33 (Q3d d0-33), or on days of radiation therapy (Days 0, 1, 2, 3, 4, 7, 8, 9) or every third day starting on Day 6 and continuing to Day 24 (Q3d d6-24). On days where both RIVPA (SEQ ID NO. 5) and radiation was administered, RIVPA (SEQ ID NO. 5) was given 2 hours after radiation. The results of this study are shown in FIG. 1. RIVPA (SEQ ID NO. 5) treatment was most effective when administered every third day throughout the period or on days of radiation, whereas treatment starting 6 days after initiation of radiation was not beneficial (i.e., Q3d d6-24). A follow-up study was undertaken to evaluate dosing with 25 mg/kg IV RIVPA (SEQ ID NO. 5) Q3d d0-33, on days of radiation, or every third day during radiation treatment (i.e., Days 0, 3, 6 and 9). The results of this study are shown in FIG. 2. Treatment every third day during radiation was found to be optimal, likely reflecting the durability of the RIVPA (SEQ ID NO. 5) pharmacodynamic effect, coupled with the reduction of injection stress caused by fewer IV injections in these small rodents.

Figure 4:
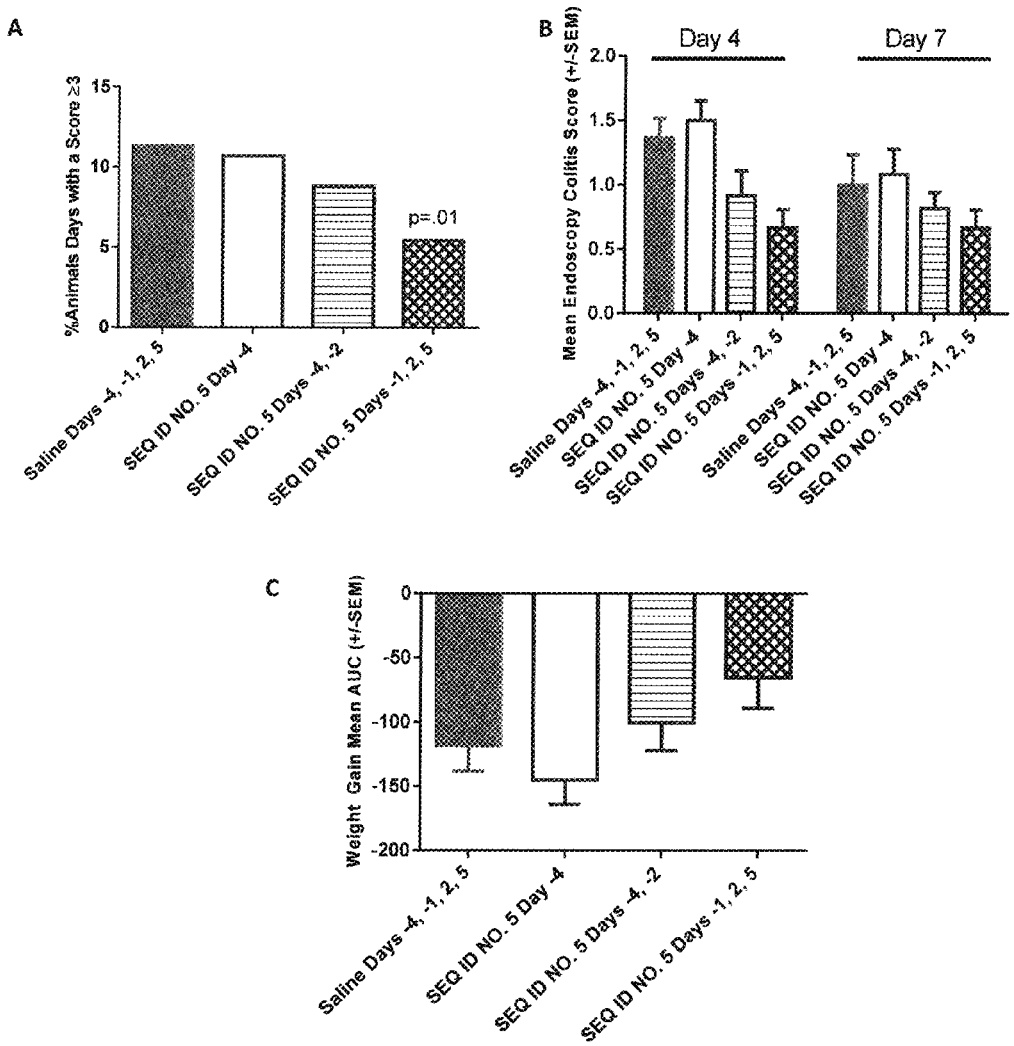
FIG. 4. RIVPA (SEQ ID NO. 5) reduces the duration of severe oral mucositis (A), severity of colitis (B) and body weight loss (C) in a chemotherapy model (First study).
Figure 5:
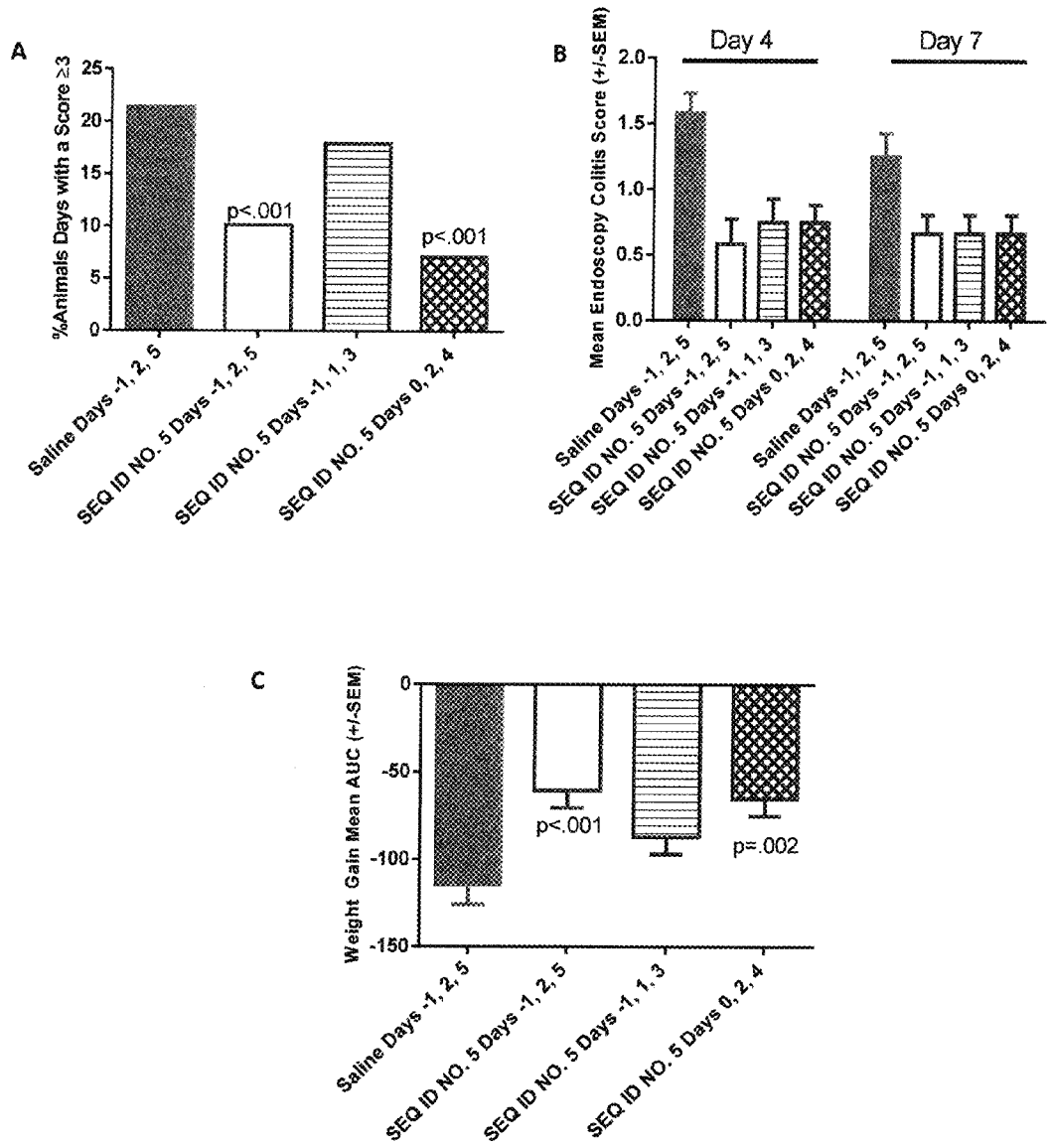
FIG. 5. RIVPA (SEQ ID NO. 5) reduces the duration of severe oral mucositis (A), severity of colitis (B) and body weight loss (C) in a chemotherapy model (Second study).
Figure 6:
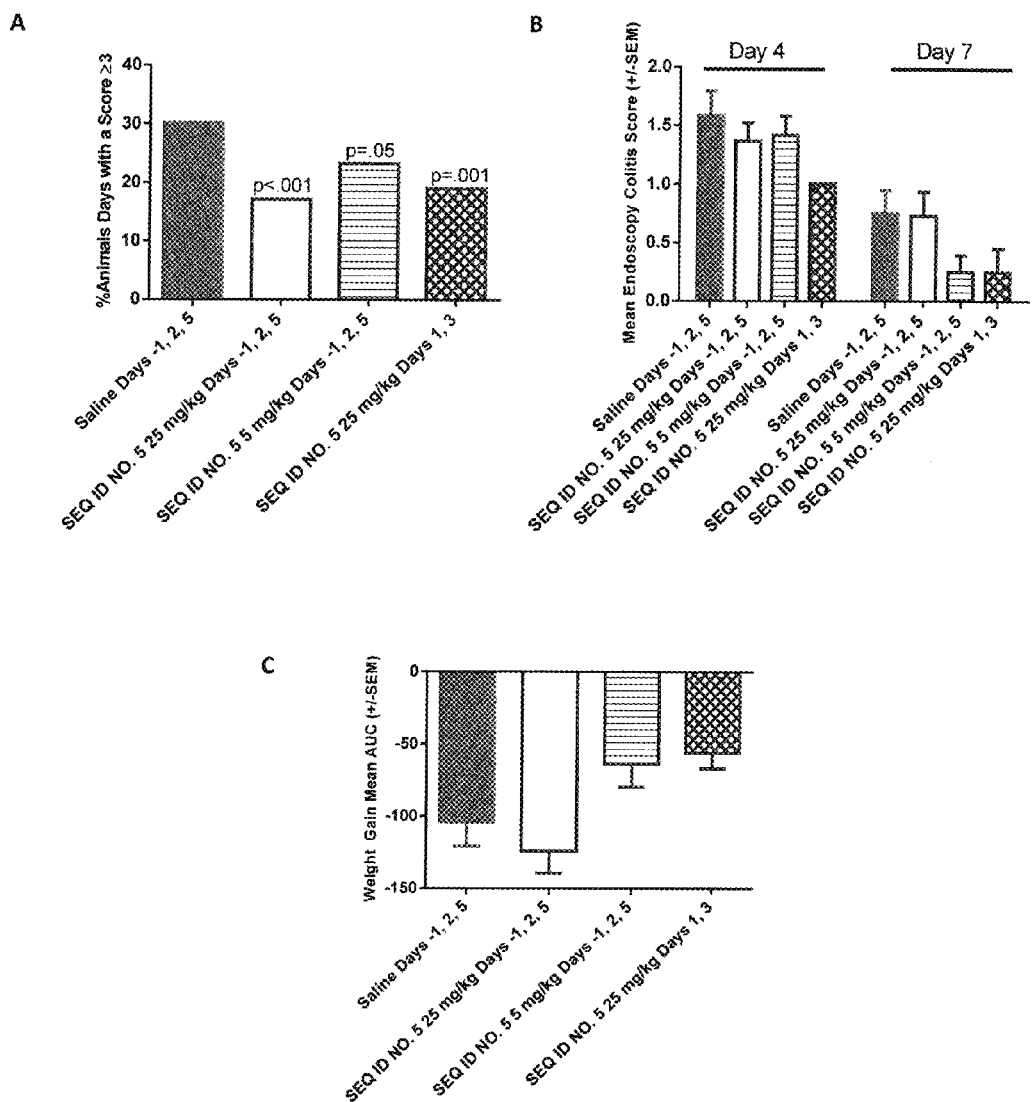
FIG. 6. RIVPA (SEQ ID NO. 5) reduces the duration of severe oral mucositis (A), severity of colitis (B) and body weight loss (C) in a chemotherapy model in a dose responsive manner.
Figure 16:
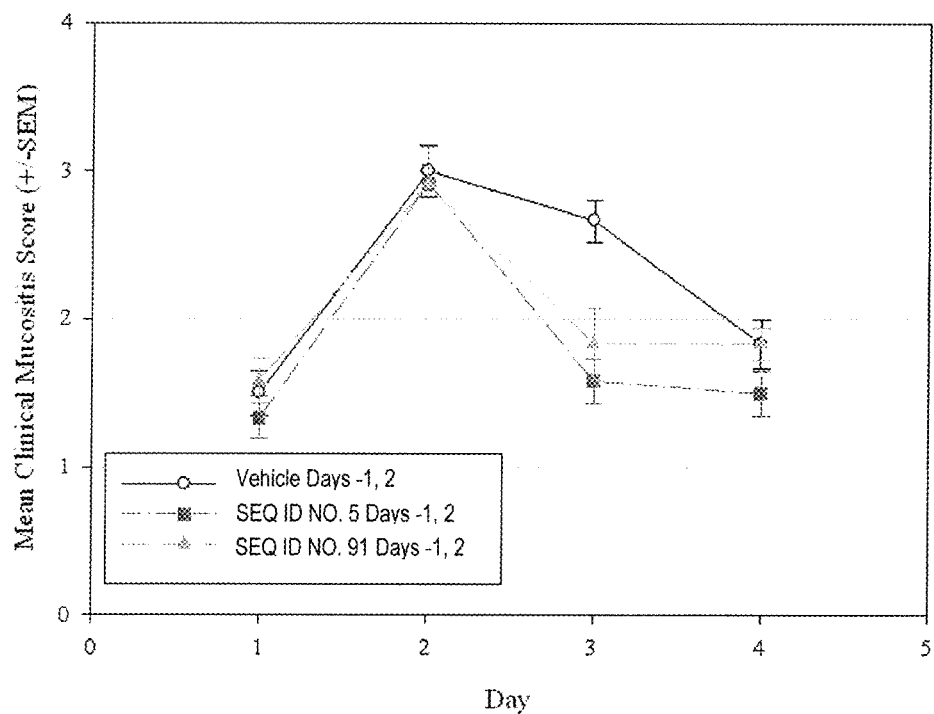
FIG. 16. R(tBg)V1KR(tBg)V2 (SEQ ID NO. 91) reduces the severity of oral mucositis in a chemotherapy model.
Figure 17:
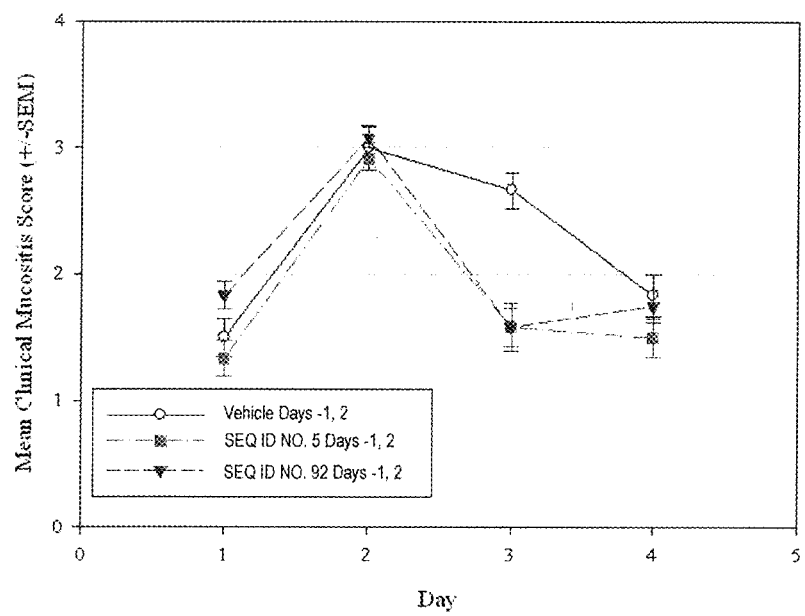
FIG. 17. RIV(mp2)A-NH2 (SEQ ID NO. 92) reduces the severity of oral mucositis in a chemotherapy model.

RIVPA (SEQ ID NO. 5) has also shown efficacy in mouse models of chemotherapy-induced oral and gastrointestinal mucositis, consistent with the response of the innate immune response to chemotherapy and/or radiation damage. In these studies, RIVPA (SEQ ID NO. 5) administration was associated with a statistically significant reduction in the duration of severe oral mucositis in a model of chemotherapy-induced mucositis in the mouse. A trend towards reduced colitis was also observed, although the mild GI damage in the control group rendered the result not statistically significant. In each study, 5-fluorouracil (60 mg/kg IP) was administered to male C3H/HeN mice on Days −4 and −2. On Day 0, a chemical burn was applied to the underside of the mouse tongue, inducing mucositis which generally peaked on Day 2. Mouse tongues were scored for mucositis daily from Days 1 to 14, with scores 23 representing severe mucositis. Body weights were also measured daily and colitis severity was determined by video endoscopy on Days 4 and 7. In the first study, RIVPA (SEQ ID NO. 5) (25 mg/kg IV) was administered either once on Day −4 immediately prior to chemotherapy, twice on Days −4 and −2 immediately after chemotherapy or 3 times on Days −1, 2 and 5. RIVPA (SEQ ID NO. 5) administration on multiple occasions throughout the period of peak mucositis damage was the most effective (i.e., on Days −1, 2 and 5). The results of this study are shown in FIG. 4. In the second study, RIVPA (SEQ ID NO. 5) (25 mg/kg IV) was administered on either Days −1, 2 and 5, Days −1, 1 and 3 or Days 0, 2, and 4. The results of this study are shown in FIG. 5. Statistically significant changes in the duration of severe mucositis (FIG. 5—panel A), the severity of colitis on Day 4 (FIG. 5—panel B) and the mean body weight loss (FIG. 5—panel C) correlated among the groups. In the third study, RIVPA (SEQ ID NO. 5) (25 or 5 mg/kg IV, as indicated) was administered either on Days −1, 2 and 5 or on Days 1 and 3. Again, the dosing regimen utilizing RIVPA (SEQ ID NO. 5) on every third day was most effective, with decreased dose levels resulting in decreased efficacy. The mucositis, colitis and body weight results from this study are shown in FIG. 6 as A, B, and C, respectively. Statistical significance was assessed for oral mucositis using a chi-square analysis and for body weight area under the curve (AUC) with an ANOVA on ranks. R(tBg)V1KR(tBg)V2 (SEQ ID NO. 91) and 92 also demonstrated efficacy in the mouse model of chemotherapy-induced mucositis, where the mucositis scores were evaluated for 4 days after induction of mucositis (FIG. 16, FIG. 17). Treatment with R(tBg)V1KR(tBg)V2 (SEQ ID NO. 91) and RIV(mp2)A-NH2 (SEQ ID NO. 92) was administered on Days −1 and 2 at a dose of 25 mg/kg IV.

Efficacy in Response to Radiation Damage

RIVPA (SEQ ID NO. 5) and other IDRs modulate the innate defense response to tissue injury, reducing the severity of damage caused by the inflammatory cascade and enhancing resolution of disease. As described above, IDRs can mitigate the response to radiation damage in an oral mucositis model (FIG. 1, FIG. 2). In another model, assessing the prevention of radiation-induced mucositis (25 Gy administered to the mouse snout on Day 0), RIVPA (SEQ ID NO. 5) (5 doses of 25 mg/kg administered IV every second day) did not have any significant impact on disease progression. Progressive thinning of the mouse tongue was assessed on Days 0, 2, 4, 6, 8, and 10 by histopathological analysis of the number of basal and suprabasal apoptotic, mitotic and total epithelial cells per unit area and per unit length. It is noted that the dose of radiation used (25 Gy) was chosen such that progressive thinning of the tongue epithelium was observed but no overt mucositis occurred. This result demonstrates the lack of proliferative potential of RIVPA (SEQ ID NO. 5), and suggests that RIVPA (SEQ ID NO. 5) effects are only observable once the relevant pathways are stimulated by overt tissue damage or pathogen invasion.

Efficacy in the Gastrointestinal Tract

Figure 3:
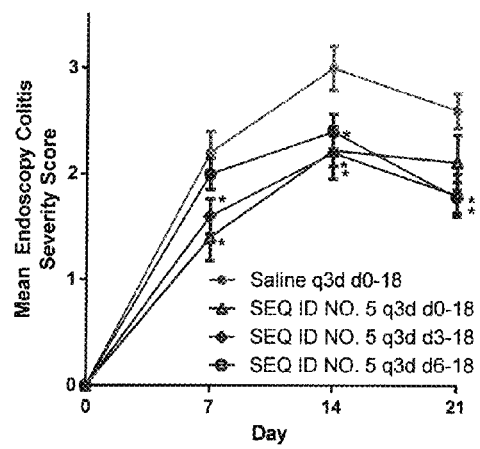
FIG. 3. RIVPA (SEQ ID NO. 5) reduces the severity of DSS-induced colitis as measured by endoscopy on days 7, 14, and 21 (A) and histopathology on day 21 (B,C,D).
Figure 3:
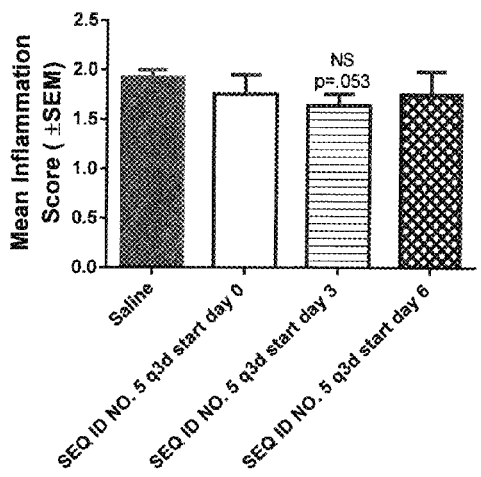
Figure 3:
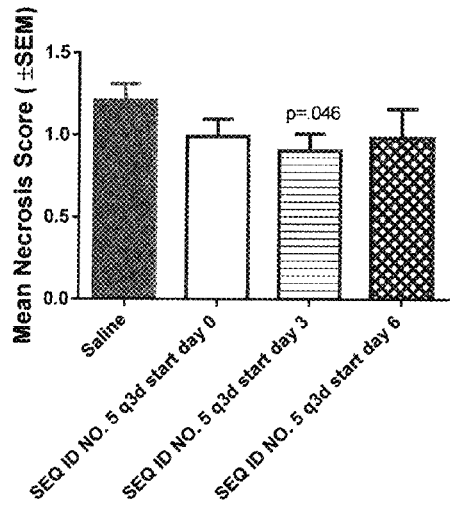
Figure 3:
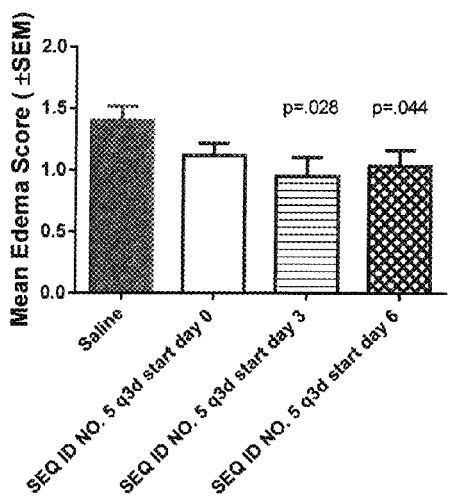

The ability of IV RIVPA (SEQ ID NO. 5), administered pre-emptively or therapeutically, to directly protect GI mucosal surfaces was confirmed in a DSS-induced colitis model. In this model, DSS was administered as a 3% DSS solution in the drinking water of male C57BL/6 mice from Days 0 to 5 of the study. Colitis was monitored by video endoscopy on Days 7, 14 and 21. RIVPA (SEQ ID NO. 5) (25 mg/kg IV) was administered every third day from Days 0 to 18 (Q3d d0-18), from Days 3 to 18 (Q3d d3-18) or from Days 6 to 18 (Q3d d6-18). The results of the study are shown in FIG. 3. By Day 14, all RIVPA (SEQ ID NO. 5) treatment regimens demonstrated a statistically significant reduction in endoscopic colitis severity score. However, reduction in Day 7 scores was only observed in groups which had received at least 2 doses of RIVPA (SEQ ID NO. 5) by that time (i.e., Q3d d0-18 and Q3d d3-18 but not Q3d d6-18). On Day 21, all 3 treatment groups appeared to be responding in a similar manner. Histopathology of the colon on Day 21 indicated that some RIVPA (SEQ ID NO. 5) treated groups had statistically significantly decreased edema and necrosis, whereas other RIVPA (SEQ ID NO. 5) treated groups had similar responses which did not reach statistical significance. Statistical analysis was undertaken using t-tests and an asterisk indicates statistically significant differences from control (p<0.05).

As described above, IDRs are also able to reduce the duration and/or severity of gastrointestinal mucositis in a chemotherapy-induced mucositis model (FIG. 4, FIG. 5, FIG. 6).

Efficacy in Infected Animals

RIVPA (SEQ ID NO. 5) reduces bacterial burden and improves survival in the presence or absence of antibiotic treatment in various murine infection models, with consistent efficacy at dose levels of 25 mg/kg IV and higher and with an enduring pharmacodynamic effect of up to 5 days. RIVPA (SEQ ID NO. 5) efficacy is complementary to antibiotic treatment in both normal and immune compromised mice. Efficacy of RIVPA (SEQ ID NO. 5) has been demonstrated against disease caused by Gram-positive (*S. aureus* and MRSA) and Gram-negative (*Klebsiella*, *E. coli* and *B. pseudomollei*) Infections.

*S. aureus*

RIVPA (SEQ ID NO. 5) has been tested both in combination with vancomycin treatment and as a stand-alone treatment.

Figure 7:
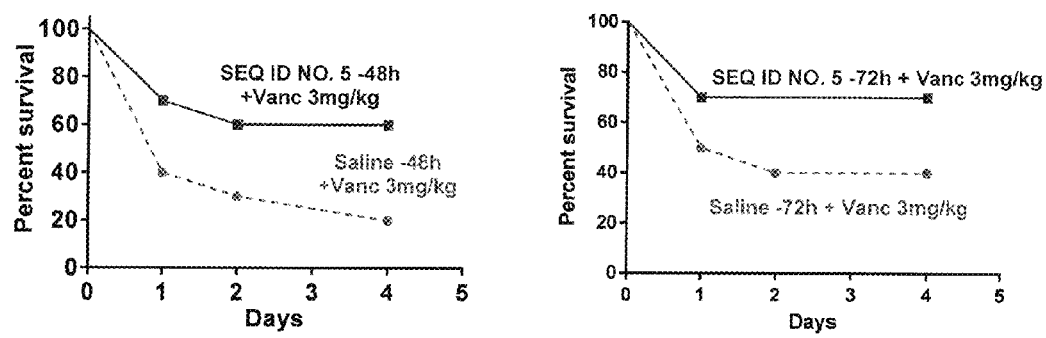
FIG. 7. Combination of RIVPA (SEQ ID NO. 5) and Vancomycin treatment in an MRSA IP infection model.
Figure 8:
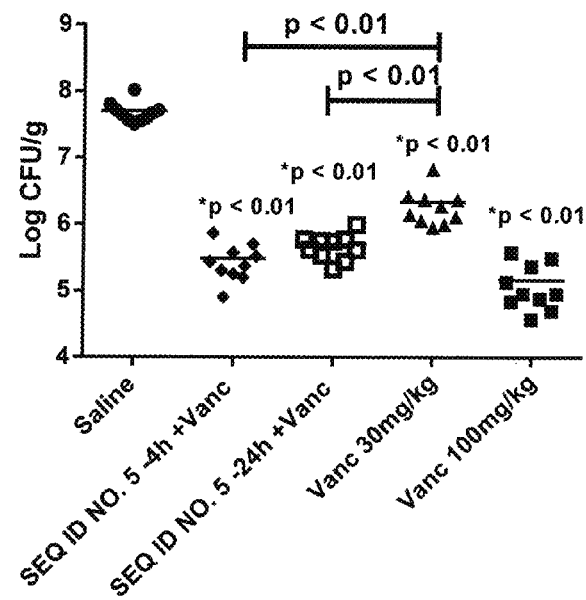
FIG. 8. RIVPA (SEQ ID NO. 5) activity in neutropenic mice in the thigh abscess MRSA infection model.

RIVPA (SEQ ID NO. 5) treatment increased survival in a MRSA peritoneal infection model when administered in combination with a sub-optimal antibiotic dose of vancomycin (Study #: D-7-E-11). RIVPA (SEQ ID NO. 5) (50 mg/kg) or saline treatment was administered IV either 48 or 72 h prior to inoculation with MRSA (UC6685; $8.2 \times 10^7$ colony forming units [cfu]) to female CF-1 mice (N=10/group). Vancomycin treatment (3 mg/kg) was administered subcutaneously (SC), 1 and 5 h after infection. Survival was monitored once daily for 5 days. The results of this study are shown in FIG. 7.

Figure 9:
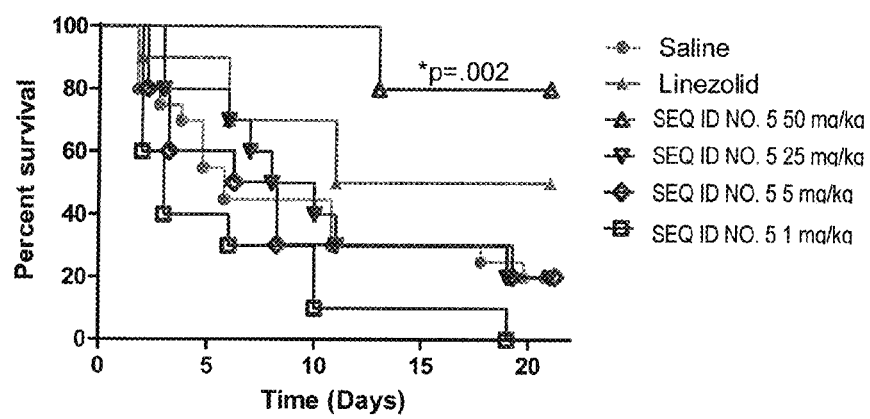
FIG. 9. Dose response of RIVPA (SEQ ID NO. 5) in the MRSA bacteremia model in immunocompetent mice.
Figure 10:
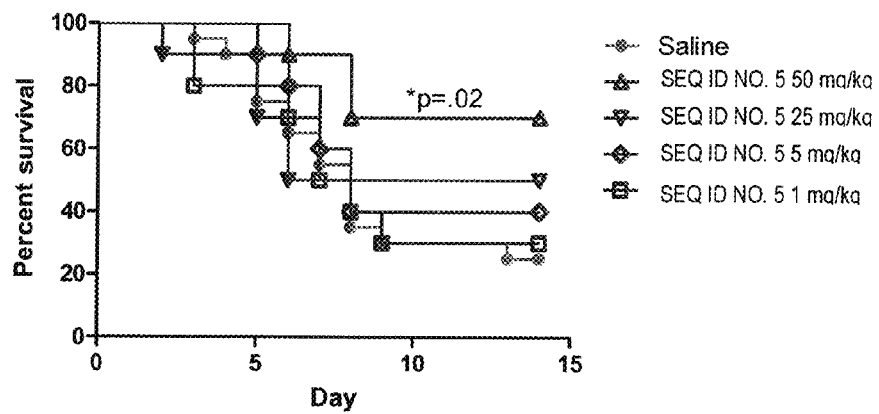
FIG. 10. Dose response of RIVPA (SEQ ID NO. 5) in the MRSA bacteremia model in mice lacking T-cells.

RIVPA (SEQ ID NO. 5) is also effective when administered by itself. Multiple studies with IV administered RIVPA (SEQ ID NO. 5) were conducted in a MRSA bacteremia model. RIVPA (SEQ ID NO. 5) administration demonstrated a dose response in this model in either immunocompetent Balb/c mice or nu/nu mice lacking T-cells, with a single dose of 50 mg/kg resulting in statistically significant enhanced survival over the saline control. In the first study, MRSA (USA300, 7.3 log 10 cfu) was administered via IV injection into the tail vein of female Balb/c mice at time 0. Four hours prior to infection, a single dose of saline or RIVPA (SEQ ID NO. 5) at the indicated dose levels was injected IV into the tail vein. Sub-optimal antibiotic treatment (linezolid, 6.25 mg/kg) was administered once orally immediately after infection. Survival was monitored for 21 days after the infection. The results of this study are shown in FIG. 9. In the second study, RIVPA (SEQ ID NO. 5) (IV) or saline (IV) was administered once 4 h prior to infection with MRSA (strain USA300, $7.0 \log_{10}$ cfu) via the tail vein into female nu/nu mice. Survival was monitored for 14 days, as shown in FIG. 10. Statistically significant differences (i.e., p≤0.05) in survival were found with the 50 mg/kg dose level as assessed using Kaplan Meier analysis of each treatment group relative to the saline control.

In summary, investigations using stand-alone IV RIVPA (SEQ ID NO. 5) treatment in various *S. aureus* infection studies have demonstrated that:

The effects of RIVPA (SEQ ID NO. 5) are dose dependent between 1 and 50 mg/kg in mouse, with dose levels of 25 mg/kg and higher consistently demonstrating efficacy (Table 2; FIG. 9 and FIG. 10). This dose level was also effective in the more chronic disease context available in injury models (FIG. 1 to FIG. 6).

TABLE 2

Rate of Successful Treatment of *S. aureus* Infection with a Single IV RIVPA (SEQ ID NO. 5) Treatment as a Function of Dose Level

| RIVPA (SEQ ID NO. 5) Dose Level (mg/kg) | % Successful Treatments[i] Any Dose Schedule (# tested groups) | % Successful Treatments RIVPA (SEQ ID NO. 5) administered 4 h prior to infection (# studies) |
|---|---|---|
| 50[ii] | 100 (N = 4) | 100 (N = 2) |
| 25[iii] | 67 (N = 6) | 50 (N = 4) |
| 5[iv] | 42 (N = 12) | 33 (N = 6) |
| 1[v] | 0 (N = 2) | 0 (N = 2) |

[i]Successful treatments demonstrated at least a 20% increase in survival over the relevant saline control.
[ii]Study #: TPS-8-B-100, TPS-8-B-150, TPS-8-B-116, D-7-E-9
[iii]Study #: TPS-8-B-100, TPS-8-B-150, TPS-8-B-120, TPS-8-B-112
[iv]Study #: TPS-8-B-100, TPS-8-B-150, TPS-8-B-116, TPS-8-B-114, TPS-8-B-120, TPS-8-B-101
[v]Study #: TPS-8-B-100, TPS-8-B-150

Daily dosing of RIVPA (SEQ ID NO. 5) is not required and dosing every $2^{nd}$ or $3^{rd}$ day is sufficient in the more chronic disease context available in Injury models, it was further confirmed that dosing every $3^{rd}$ day appears to be optimal (data not shown).

RIVPA (SEQ ID NO. 5) can be administered up to 24 h after the initiation of Infection in the MRSA bacteremia model and still confer a survival benefit (data not shown). Hence its action is rapid.

Depending on dose level, a single dose of RIVPA (SEQ ID NO. 5) can be administered up to 5 days prior to the initiation of infection and still confer a survival benefit (data not shown), reflecting the durable pharmacodynamic impact of RIVPA (SEQ ID NO. 5) despite its rapid pharmacokinetic (PK) clearance (within minutes) from the circulation of mice.

The survival benefit conferred by RIVPA (SEQ ID NO. 5) treatment can be sustained for at least 21 days (FIG. 9).

Figure 18:
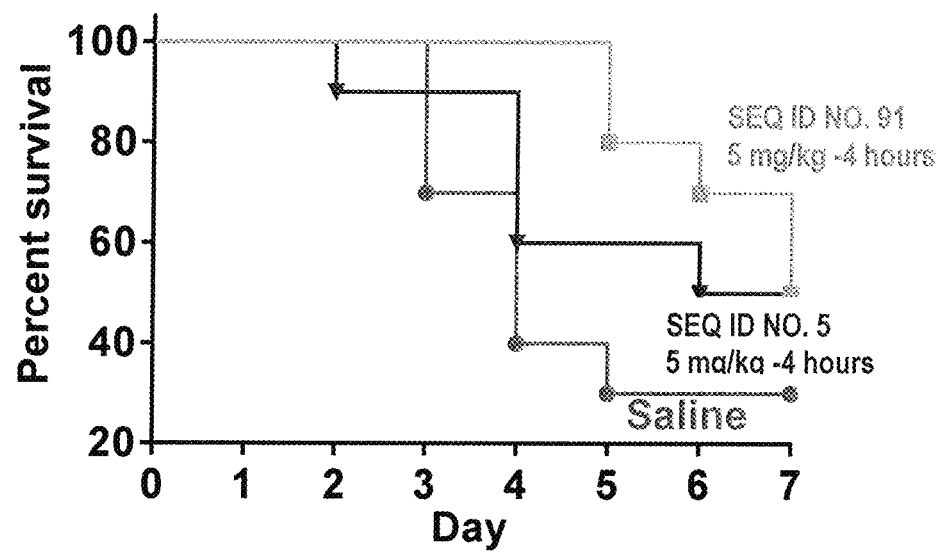
FIG. 18. R(tBg)V1KR(tBg)V2 (SEQ ID NO. 91) enhances survival in an MRSA bacteremia model.
Figure 19:
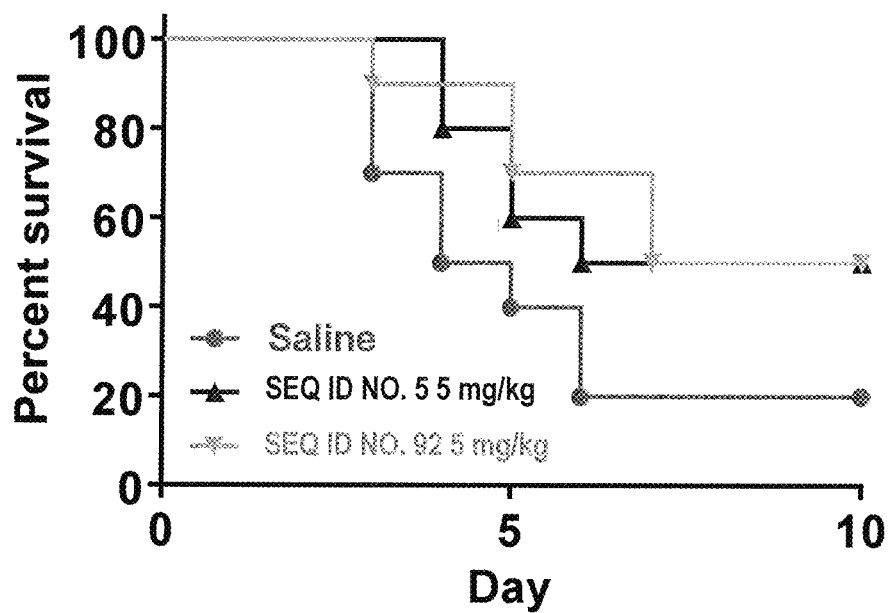
FIG. 19. RIV(mp2)A-NH2 (SEQ ID NO. 92) enhances survival in an MRSA bacteremia model.

RIVPAY* (SEQ ID NO. 90) and R(tBg)V1KR(tBg)V2 (SEQ ID NO. 91) (5 mg/kg administered 4 hours prior to infection) also improve survival in an MRSA bacteremia model (FIG. 18; FIG. 19).

Figure 11:
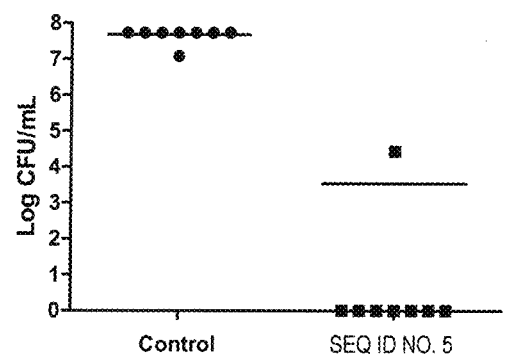
FIG. 11. Therapeutic RIVPA (SEQ ID NO. 5) efficacy in the S. aureus acute peritoneal infection model.

Local administration of RIVPA (SEQ ID NO. 5) has also been demonstrated to be effective when the administration is local to the site of infection. In a Gram-positive peritoneal infection model in mouse, RIVPA (SEQ ID NO. 5) significantly reduced the bacterial load by over 7 logs (Study #: D-7-E-14). Intraperitoneal (IP) injection of *S. aureus* (Catalog No. 25923, ATCC, $6 \times 10^7$ cfu) with 5% mucin was administered IP to female CD-1 mice (N=8/group) and RIVPA (SEQ ID NO. 5) (9.5 mg/kg) was injected IP 4 h later. Mice were sacrificed 24 h after infection and peritoneal lavage fluid was assessed for bacterial counts. The results of this study are shown in FIG. 11 (each data point represents the result from an individual mouse—dead mice were given the highest bacterial count of any mouse obtained in the study and are represented as open symbols in the graph).

Figure 12:
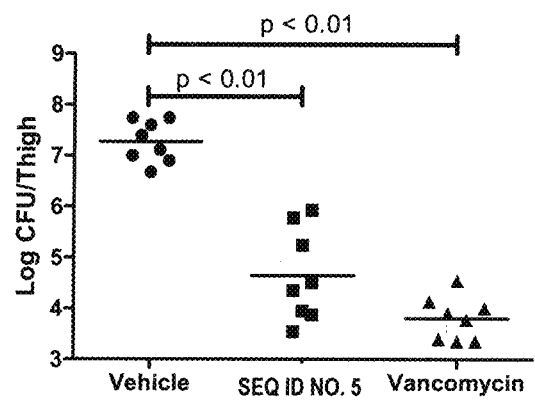
FIG. 12. RIVPA (SEQ ID NO. 5) activity in neutropenic mice in the thigh abscess S. aureus infection model.

RIVPA (SEQ ID NO. 5) also significantly reduced bacterial load in neutropenic mice in an *S. aureus* thigh abscess infection model when administered as a local intramuscular (IM) injection. Female Swiss albino mice (N=8/group) were rendered neutropenic by treatment with Cp (100 mg/kg), 3 and 1 days before IM infection with *S. aureus* (Catalog No. 29213, ATCC, ~$9.5 \times 10^5$ cfu). RIVPA (SEQ ID NO. 5) (50 mg/kg) was administered IM 24 h prior to infection and vancomycin (100 mg/kg) was administered SC at 1, 6 and 18 h after infection. The number of bacterial cfu present in the infected thigh was assessed 24 h after Initiation of infection in each group. The results of this study are shown in FIG. 12.

Klebsiella

Figure 13:
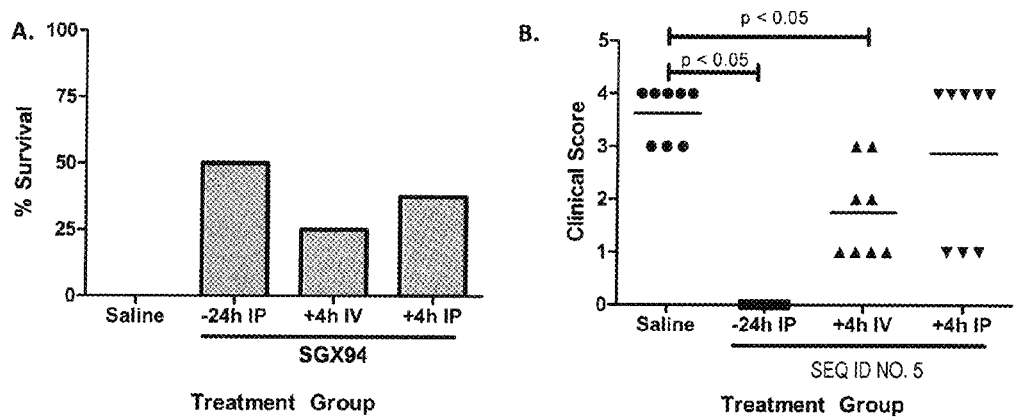
FIG. 13. RIVPA (SEQ ID NO. 5) efficacy in a Klebsiella peritoneal infection model with high (A) and low (B) bacterial infection. *Absence of a bar in (A) indicates all mice died (0% survival).

RIVPA (SEQ ID NO. 5) increased survival in a Gram-negative peritoneal infection model when administered either locally (IP) or systemically (IV). Of note, systemic administration appeared as good or better than local administration. RIVPA (SEQ ID NO. 5) treatment (24 mg/kg) was administered either IP (24 h prior to infection or 4 h post-infection) or IV (4 h post-infection) to female Balb/c mice (N=8/group) inoculated with *Klebsiella pneumoniae* (Catalog No. 43816, ATCC) at either $2.8 \times 10^5$ cfu (FIG. 13—panel A) or $5.3 \times 10^2$ cfu (FIG. 13—panel B) and survival was monitored over 24 h. The protective effects of RIVPA (SEQ ID NO. 5) in this context are shown in FIG. 13. A survival endpoint is shown for animals receiving the higher inoculum of bacteria (panel A). All animals receiving the lower inoculum survived in all groups (panel B) and were assessed for clinical signs (e.g., piloerection, decreased movement, hunched abdomen, etc.) 24 h after infection; these are summarized as clinical scores.

Efficacy in Skin Damage

Figure 14:
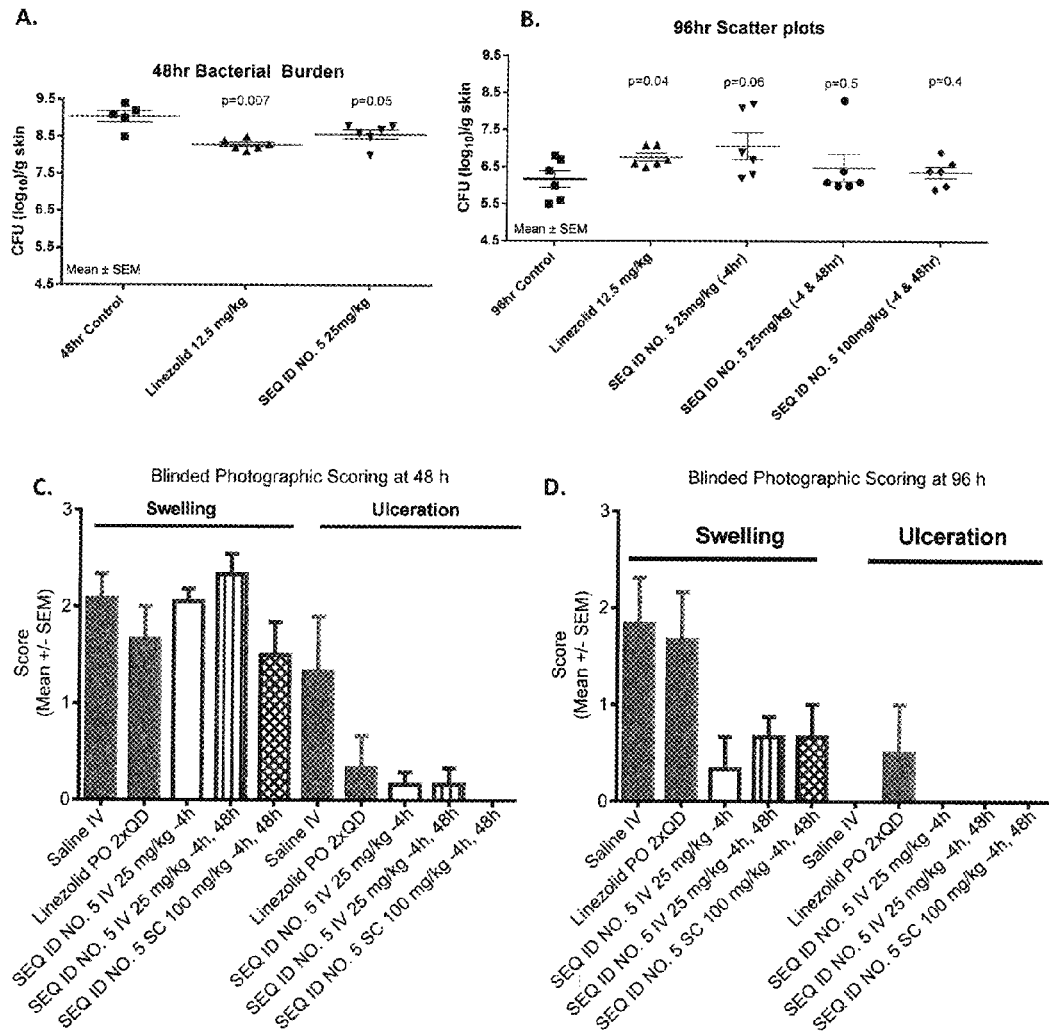
FIG. 14. RIVPA (SEQ ID NO. 5) enhances resolution of tissue damage in topically MRSA-infected skin. 48 h Bacterial Burden (A), 96 h Scatter plot (B), Blinded Photographic Scoring at 48 h (C), Blinded Photographic Scoring at 96 h (D). *Absence of a bar in (C) and (D) indicates all mice had a zero score, yielding a mean and standard error of the mean (SEM) of 0±0.

Systemically administered RIVPA (SEQ ID NO. 5) is also efficacious in the case of skin injury and infection, accelerating skin healing in an MRSA skin infection model. Infection was initiated 1 day after the hair was removed from the dorsal area of each mouse. RIVPA (SEQ ID NO. 5) (25 mg/kg IV or 100 mg/kg SC) was administered 4 h prior to infection and at various times after infection as indicated. Oral linezolid was used as the comparator and was administered daily at 12.5 mg/kg. On Day 0 (at −1 h) each mouse was anesthetized using isoflurane and the shaved dorsal skin was damaged by 7 consecutive applications and removals of surgical tape. This lesion was then immediately infected by topical administration of 10 μL of the bacterial suspension, delivering a total challenge of 7.6 $\log_{10}$ cfu per mouse. Efficacy was evaluated by measurement of the bacterial burden in punch biopsies of the skin at 48 h (FIG. 14—panel A) and 96 h (FIG. 14—panel B) following the bacterial challenge and by macroscopic assessment of digital images of the skin by a blinded, board-certified pathologist at 48 h (FIG. 14—panel C) and 96 h (FIG. 14—panel D) after infection. Of note, neither linezolid nor RIVPA (SEQ ID NO. 5) reduced bacterial load in the biopsies at 48 or 96 h relative to control, although the localization of any of the isolated bacteria (i.e., on the skin surface or within the tissue) was not determined. Nevertheless, wound healing clearly occurred. The mean bacterial burden for each therapeutic group was statistically compared to that of its time-matched saline control through use of a t-test comparison of means, assuming unequal variances, performed on Excel. Comparisons which returned a p value≤0.05 were considered statistically different.

Safety Pharmacology in Healthy Animals:

Two pilot and 2 definitive repeat-dose toxicity studies were conducted with RIVPA (SEQ ID NO. 5) in mice and cynomolgus monkeys using the intravenous (IV; slow bolus) route of administration. All studies were conducted by LAB Research Inc., Canada.

Non-GLP pilot toxicology studies indicated that the maximum tolerated dose (MTD) of a single administration of RIVPA (SEQ ID NO. 5), administered as an IV injection over 30 to 60 seconds, is 88 mg/kg (actual dose) in mouse. In non-GLP pilot studies in nonhuman primates (NHP), mild clinical signs (shallow/labored respiration, decreased activity, partially dosed eyes and muscle twitches) were noted in 1 or both animals after administration of 90 (1 animals), 180 (both animals) and 220 (1 animal) mg/kg RIVPA (SEQ ID NO. 5) during and shortly after dosing. These resolved within a few minutes without detectable residual effects.

The safety of multiple daily injections of RIVPA (SEQ ID NO. 5) has also been evaluated in GLP studies in mice and cynomolgus monkeys. In mouse, doses of 20, 60, or 90 mg/kg/day were given IV for 14 days. Deaths were observed at the high dose, preceded mainly by labored respiration and recumbancy. Lethality was also observed in 1 animal given 60 mg/kg but no other animals exhibited clinical signs at this dose. No test article-related mortality or clinical signs were observed at 20 mg/kg. In survivors of all groups, there was no evidence of toxicity in any organ or abnormal biochemistry or hematology. No adverse effects were observed at 20 mg/kg for 14 days.

RIVPA (SEQ ID NO. 5) at 20, 80, 160 mg/kg/day was given IV to cynomolgus monkeys for 14 days. Transient decreased activity and partially closed eyes continued to be observed during and shortly after dosing at 160 mg/kg for the first 3 days in most animals, then sporadically throughout the remaining dosing period. In all cases, these clinical signs resolved within a few minutes. No adverse effects were observed on any other measured parameter or microscopically in any tissue. The administration of RIVPA (SEQ ID NO. 5) at doses of 20 and 80 mg/kg/day did not result in any evidence of toxicity. A dose level of 80 mg/kg/day was considered to be the No-Observed-Adverse-Effect-Level (NOAEL) for this study.

No effects of RIVPA (SEQ ID NO. 5) have been observed on the central nervous system (CNS) in any study at any dose level and little or no radiolabelled RIVPA (SEQ ID NO. 5) was found in the mouse CNS at dose levels of either 20 or 90 mg/kg. No interaction was detected between RIVPA (SEQ ID NO. 5) and a battery of CNS receptors and ion channels in vitro.

A cardiovascular (CV)/pulmonary study in cynomolgus monkey using single IV doses of 20 or 80 mg/kg revealed no cardiovascular effects or changes in electrocardiogram (ECG) parameters. No respiratory effects were observed at doses of 20 or 80 mg/kg. At a dose of 80 mg/kg in this study, RIVPA (SEQ ID NO. 5) was associated with transient drooping eye lids and prostration during dosing. At 220 mg/kg, the administration of RIVPA (SEQ ID NO. 5) was associated with transient, severe clinical signs such as drooping eye lids, tremor, prostration, paleness, convulsion and collapse. In 1 animal, the high dose caused a marked reduction in respiratory rate followed by bradycardia, hypotension and death.

Overall, the NOAEL is considered to be 80 mg/kg/day for cynomolgus monkeys since transient clinical signs were limited to a single study and occurred in only 2 instances of the 98 administrations of the drug at this dose level.

No carcinogenicity, mutagenicity or reproductive toxicity studies have been conducted with RIVPA (SEQ ID NO. 5).

The effect of RIVPA (SEQ ID NO. 5) on the Innate defense system is highly selective. Consistent with these findings, no changes were observed in immune-related organ weights, histopathology, hematology and clinical chemistry during mouse and NHP 14-day toxicity studies. In the latter study, no effect on T-cell, B-cell or NK-cell counts was observed after 14 days of intravenous RIVPA (SEQ ID NO. 5) dosing in the NHP. RIVPA (SEQ ID NO. 5) did not promote the proliferation of either mouse or human normal blood cells in vitro, nor of primary human leukemia cells in vitro. Collectively, there is no indication of a potential for RIVPA (SEQ ID NO. 5) to cause immunotoxicity or non-specific immune activation. No hyperactivation or suppression of adaptive immune responses, or other impact on the phenotypes of cells associated with adaptive immunity, has been detected following RIVPA (SEQ ID NO. 5) administration.

In summary, the major toxicological finding was an acute-onset respiratory depression, accompanied by labored breathing, recumbency and transient decreased activity. At its most severe, the acute toxicity resulted in death. Clinical signs were all reversible when dosing was discontinued and animals were observed to recover within minutes, with no subsequent adverse sequellae of clinical symptoms or toxicological findings. A cardiovascular/pulmonary safety pharmacology study in nonhuman primates confirmed no cardiac toxicity or QT prolongation was occurring.

The observed respiratory depression occurred at different dose levels in different species, and was not predicted by allometric scaling. In particular, the mouse appeared to be the most sensitive species with acute toxicity occurring rarely at 60 mg/kg (HED: ~5 mg/kg) and commonly at 90 mg/kg (HED: ~7 mg/kg). In contrast in NHP (cynomolgus monkey), acute toxicity occurred occasionally at 160 mg/kg (HED: ~50 mg/kg) and consistently at 240 mg/kg (HED: ~78 mg/kg). Further studies with RIVPA (SEQ ID NO. 5) analogs in acute mouse toxicity studies have indicated that the toxicity is related to the charge but not the specific structure (amino acid sequence) or target protein binding status of the molecule, suggesting that the acute toxicity is due to a high instantaneous concentration of a charged molecule that scales with blood volume as opposed to allometrically. Moreover, mechanistic studies in mice have indicated that the respiratory depression is due to altered activity of the phrenic nerve.

Figure 15:
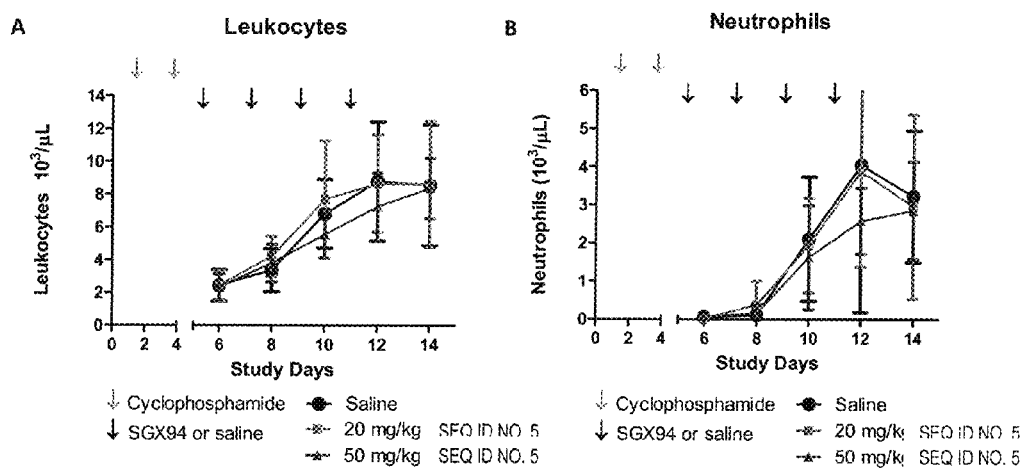
FIG. 15. Lack of RIVPA (SEQ ID NO. 5) on recovery of circulating blood cell leukocytes (A) or neutrophils (B) after induction of leukopenia in CD-1 mice.

Safety Pharmacology for Leukopenia and/or Infection:

In a non-GLP pharmacology study, RIVPA (SEQ ID NO. 5) did not alter the recovery of circulating blood cell populations after the induction of leukopenia in CD-1 mice. Leukopenia was induced with 2 IP injections of Cp (150 mg/kg on Day 1 and 100 mg/kg on Day 4), resulting in well-established leukopenia by Day 4 that persisted until approximately Day 10. Saline or RIVPA (SEQ ID NO. 5) (20 or 50 mg/kg) was administered IV on Days 5, 7, 9 and 11. Six animals per group were sacrificed on each of Days 6, 8, 10, 12 and 14 and evaluated for complete blood count and differential. Neither the levels nor dynamics of the total leukocyte and differential white blood cell counts were altered during the course of recovery when compared to the vehicle control group (FIG. 15).

Infection studies in leukopenic animals have revealed no interference of RIVPA (SEQ ID NO. 5) with antibiotic efficacy.

The lack of RIVPA (SEQ ID NO. 5) processing by, or inhibition of, CYP450 enzymes, the primary metabolism of RIVPA (SEQ ID NO. 5) by proteases throughout body tissues and the very minor role played by urine, feces and bile excretion in RIVPA (SEQ ID NO. 5) clearance suggests that pharmacokinetic drug-drug interactions will be minimal.

iv. Clinical Experience

Clinical experience with RIVPA (SEQ ID NO. 5) was obtained in a Phase 1 Study. The primary objective of the study was to determine the maximum tolerated dose (MTD) of single and repeat ascending doses of RIVPA (SEQ ID NO. 5) injectable solution following IV administration in healthy volunteers. The secondary objectives of this study included the assessment of the dose limiting toxicity (DLT), safety, PK and pharmacodynamic (PD) profiles of RIVPA (SEQ ID NO. 5) after single and repeated ascending IV doses of RIVPA (SEQ ID NO. 5). The study was divided into 2 phases: a single-ascending dose (SAD) phase and a multiple-ascending dose (MAD) phase.

Human Safety

Single IV doses of RIVPA (SEQ ID NO. 5) were well tolerated up to the maximum tested (8 mg/kg) and daily IV doses were well tolerated up to the maximum tested (6.5 mg/kg for 7 days). There were no dose limiting toxicities (DLTs) and the MTD was not reached in either phase of the trial. There were no deaths and no clinically significant, severe, or serious Adverse Events (AEs) reported during the study. No safety concerns or significant differences in mean values or changes from baseline were observed for vital sign measurements, clinical laboratory or electrocardiogram (ECG) results between drug-treated and placebo control subjects.

Single Ascending Dose Phase:

The incidence of TEAEs for those subjects who received RIVPA (SEQ ID NO. 5) was not dose-related and events did not occur at a clinically significant higher rate for subjects who received RIVPA (SEQ ID NO. 5) compared to those who received placebo. The most frequently reported TEAEs (observed in more than one subject who received RIVPA (SEQ ID NO. 5) and in a higher proportion (%) than placebo subjects) were study treatment procedure-related events (General Disorders and Administration Site Conditions) such as vessel puncture site haematoma, vessel puncture site reaction and vessel puncture site pain. All vessel puncture-related events were mild and determined to be unrelated to study treatment by the QI. The second most frequently reported TEAEs were Nervous System Disorders, specifically headache and dizziness; these events were only mild to moderate. All other TEAEs were reported by only 1 subject at any given dose level (maximum of 3 dose levels). No clinically significant trends in the nature or duration of TEAEs were demonstrated for any study cohort.

Multiple Ascending Dose Phase:

The highest incidence of TEAEs was observed at the 2 highest dose levels (4.5 and 6.5 mg/kg/day). The incidence of "possibly-related" events was also higher in the 2 highest dose levels. However, due to the small sample sizes (4 subjects received active treatment in each cohort), it was not possible to conclude whether the results definitely represented a dose-response. The majority of the TEAEs were not related to study treatment and were mild in severity with only one event reported as moderate. The most frequently reported TEAEs for subjects who received RIVPA (SEQ ID NO. 5) were General Disorders and Administration Site Conditions (i.e., procedure-related events) such as vessel puncture site haematoma, vessel puncture site reaction, and vessel puncture site pain. All vessel puncture-related events were mild and judged to be unrelated to treatment. Increased alanine aminotransferase (ALT) and back pain were reported by 3 (15.0%) subjects who received RIVPA (SEQ ID NO. 5) and these events were observed by only one (10.0%) subject who received the placebo.

Human Pharmacokinetics

Following IV administration in human subjects and consistent with findings in animal studies, RIVPA (SEQ ID NO. 5) is cleared from the circulation within minutes. In the single-dose phase of a healthy volunteer Phase 1 trial, RIVPA (SEQ ID NO. 5) was rapidly eliminated, with plasma levels decreasing to less than 10 percent of the maximum concentration (Cmax) within 9 min after the start of the 4-minute IV infusion. Following the rapid decline, a slower elimination phase was observed. The mean time of maximum concentration (Tmax) ranged between ~4 min and ~4.8 min after the start of infusion for the dose range of 0.15 mg/kg to 8 mg/kg. Maximum plasma concentrations and total exposure levels were dose-proportional and clearance of RIVPA (SEQ ID NO. 5) from the circulation was rapid, consistent with the mouse and NHP experience.

In light of the high clearance and short elimination half-life, accumulation following daily injection was not expected to occur. In the multiple-dose Phase 1 study, RIVPA (SEQ ID NO. 5) was administered daily for 7 days and the pre-dose concentrations measured on Days 5, 6, 7, as well as on Day 8 (24 h after the start of infusion on Day 7) were below the lower limit of quantitation (LLOQ) for all of the subjects.

Human Pharmacodynamics

In ex vivo investigations using blood samples obtained during the Phase 1 healthy human volunteer study, a number of cytokine and chemokine analytes were quantified after 4 hours of in vitro stimulation of whole blood with LPS. The inter-individual variability in analyte levels was larger than any variation in time or response to RIVPA (SEQ ID NO. 5) or placebo administration and the data were therefore self-normalized using the individual pre-dose analyte level to standardize all responses for each individual subject (the Activity Ratio). RIVPA (SEQ ID NO. 5) effects on the analyte Activity Ratios (ARs) were neither constant throughout time, nor linearly dose responsive. Nevertheless, in the dose range 0.15-2 mg/kg, there was evidence of an increase in the "anti-inflammatory status" (i.e., higher anti-inflammatory TNF RII and IL-Ira levels coupled with lower TNFα and IL-10 levels after LPS stimulation of blood from each individual).

b. Scientific Rationale for IDR Injection

Mucositis

Mucositis has been linked to the dysregulation of the innate defense system, resulting in a cascade of inflammatory action which further damages the mucosal lining and leads to overt mucositis (Sonis, 2004). In particular, while the chemotherapy or radiation treatment causes damage to the underlying endothelium and epithelium, the response of the innate defense system to the resulting "DAMPS" results in an inflammatory cascade which exacerbates this damage. Recent studies evaluating gene expression in animals and humans pre-disposed to intense oral mucositis have supported the role of the innate defense system in the disease (Sonis, 2010). Moreover, lower gastrointestinal tract mucositis has also been attributed to similar mechanisms (Bowen, 2008).

Acute Radiation Syndrome

Acute radiation exposure is associated with damage to the epithelium (skin), bone marrow (hematopoietic syndrome) and gastrointestinal tract (GI). Moreover, mortality becomes increasingly acute as the radiation exposure increases, limiting the potential for therapeutic intervention. Early mortality (<2 weeks) after acute radiation exposure is associated with damage to the gastrointestinal tract. Acute radiation causes direct damage to stem cells within the base of the crypts of Lieberkuhn, resulting in mitotic cessation and their death through apoptotic mechanisms (Potten 1997a, Potten 1997b). The recovery and/or long-term sequellae of this damage have been demonstrated to be related to both the GI microbiota and the innate immune repair response (Crawford 2005; Garg, 2010). Ongoing studies on the radiobiology of normal and oncogenic tissue have demonstrated a significant role for the response of the innate immune system to radiation (Schaue and McBride, 2010; Lauber 2012; Burnette 2012). Moreover, agonists targeting the innate defense system (i.e., TLR-9 agonist) have been shown to be radio-protective in the GI ARS setting (Saha, 2012).

Oral and GI mucositis as a consequence of radiation tumor therapy serves as a relevant proxy for the GI component of ARS. Consistent with the function of IDRs and the role of innate defenses in mucositis, efficacy with IDRs has been demonstrated in a wide array of mucosal damage models. In particular, studies in both chemotherapy and radiation-induced oral and gastro-intestinal mucositis have revealed that IDRs can reduce the peak intensity and duration of mucositis yielding ~50% reduction in the duration of severe mucositis (FIG. 1, FIG. 2, FIG. 4, FIG. 5, FIG. 6, FIG. 7, FIG. 8, FIG. 16, FIG. 17).

Also consistent with the IDR impact on host innate immunity, efficacy in infection models has been demonstrated with both Gram-negative and Gram-positive (FIG. 9, FIG. 10, FIG. 18, FIG. 19) bacterial pathogens in both immunocompetent (e.g., FIG. 9) and immunocompromised (leukopenic or lacking T-cells) mice.

IDRs are systemically administered and impact mucosal surfaces (e.g., oral mucosa, colon [FIG. 3]) as well as the skin and is effective in both systemic (FIG. 7, FIG. 8, FIG. 9 and FIG. 10) and local Infections.

In summary, IDRs modulates the innate defense response to damage (FIG. 1 to FIG. 8, FIG. 16, FIG. 17). Specifically, RIVPA (SEQ ID NO. 5) mitigates damage incurred by radiation (FIG. 1, FIG. 2) and is systemically active, with significant protective effects observed in the gastrointestinal tract in response to chemotherapy (FIG. 3, FIG. 4, FIG. 5 and FIG. 6). Moreover, IDRs are efficacious in both immunocompetent and leukopenic animals—suggesting that the hematopoietic impacts which occur concomitantly with the GI component of ARS will not impair the efficacy of RIVPA (SEQ ID NO. 5). Given its anti-infective role, RIVPA (SEQ ID NO. 5) may also be efficacious in the hematopoletic subsyndrome of ARS, but the only direct evaluations of this have utilized sub-optimal intraperitoneal dosing. RIVPA (SEQ ID NO. 5) is not expected to pharmacokinetically interfere with concomitant therapies and has demonstrated no interference with the major classes of antibiotics (data not shown). RIVPA (SEQ ID NO. 5) does not interfere with recovery from leukopenia (FIG. 15). In combination with the demonstrated safety of RIVPA (SEQ ID NO. 5) in human volunteer studies (See 4.a.iv above), these studies strongly support the use of RIVPA (SEQ ID NO. 5) and other other IDRs treatment in response to acute radiation exposure to reduce acute mortality.

REFERENCES

Athman R, Philpott D. Innate immunity via Toll-like receptors and Nod proteins. *Curr Opin Microbiol.* 2004; 7, 25-32.

Beutler B. Innate immunity: an overview. *Mol Immunol.* 2004; 40, 845-59.

Beutler B, Hoebe K, Du X, Ulevitch R J. How we detect microbes and respond to them: the Toll-like receptors and their transducers. *J Leukoc Biol.* 2003; 74, 479-85.

Bowen J, Keefe D. New Pathways for Alimentary Mucositis. *J Oncology.* 2008; 1-7.

Burnette B, Fu Y, Weichselbaum R. The confluence of radiotherapy and immunotherapy. *Fontiers in Oncology.* 2012; 2, article 143.

Crawford P, Gordon J. Microbial Regulation of Intestinal Radiosensitivity. *PNAS.* 2005; 102(37), 13254-13259.

Doyle S L, O'Neill L A. Toll-like receptors: from the discovery of NFkappaB to new insights into transcriptional regulations in innate immunity. *Biochem Pharmacol.* 2006; 72, 1102-13.

Elting et al. *Cancer.* 2008; 113(10)2704-2713.

Foster S L, Hargreaves D C, Medzhitov R. Gene-specific control of inflammation by TLR-induced chromatin modifications. *Nature.* 2007; 447, 972-8.

Garg S, Boerma M, Wang J, Fu Q, Loose D, Kumar K, Hauer-Jensen M. Influence of a Sublethaal Total-Body Irradiation on Immune Cell Populations in the Intestinal Mucosa. *Radiat. Res.* 2010; 173(4), 469-78.

Janeway C A, Jr., Medzhitov R. Innate immune recognition. *Annu Rev Immunol.* 2002; 20, 197-216.

Lauber K, Ernst A, Orth M, Herrmann M, Belka C. Dying cell clearance and its impact on the outcome of tumor radiotherapy. *Frontiers in Oncology.* 2012; 2, Article 116.

Mateus et al. *Br. J. Dermatol.* 2009; 161(3), 515-521.

Matzinger, P. The Danger Model: A renewed sense of self. *Science.* 2002; 296(5566), 301-305.

Molloy M, Bouladoux N, Belkald Y. Intestinal Microbiota: shaping local and systemic immune responses. *Semin Immunol.* 2012; 24(1), 58-66.

Murphy. *J Supportive Oncology.* 2007; 5(9) supplement 4, 13-21.

Nonzee N J, Dandade N A, Markossian T, Agulnik M, Argiris A, Patel J D, Kern R C, Munshi H G, Calhoun E A, Bennett C L Evaluating the supportive care costs of severe radiochemotherapy-induced mucositis and pharyngitis. Cancer. 2008; 113: 1446-52.

Paris F, et al. Endothelial apoptosis as the primary lesion initiating intestinal radiation damage in mice. Science. 2001; 293(5528):293-297.

Potten C S. A comprehensive study of the radiobiological response of the murine (BDF1) small intestine. Int J Radiat Biol. 1990; 58(6):925-973.

Potten C S and Booth C. The role of radiation-induced and spontaneous apoptosis in the homeostasis of the gastrointestinal epithelium: a brief review. Comp Biochem Physiol B. 1997a; 118(3):473-478.

Potten C S, Booth C and Pritchard D M. The intestinal epithelial stem cell: the mucosal governor. Int J Exp Pathol. 1997b; 78(4):219-243.

Saha 5, Bhanja P, Liu L, Alfierl A, Yu D, Kandimalla E, Agrawal E, Guha C. TLR9 Agonist Protects Mice from Radiation-Induced Gastrointestinal Syndrome. *PLOS one.* 2012; 7(1), e29357.

Sankhala et al. *Target Oncol.* 2009; 4(2), 135-142.

Santaolalla R, Fukata M, Abreu M. Innate immunity in the small intestine. *Curr Opin Gastroenterol.* 2011; 27(2), 125-31.

Schaue D, McBride W. Links between Innate Immunity and Normal Tissue Radiobiology. *Radiat Res.* 2010; 173(4), 406-17.

Scott M G, Dullaghan E, Mookherjee N, Glavas N, Waldbrook M, Thompson A, Wang A, Lee K, Doria S, Hamill P, Yu J J, Li Y, Donini O, Guarna M M, Finlay B F, North J R, Hancock R E W. An anti-Infective peptide that selectively modulates the innate immune response. Nat Biotechnol 2007; 25: 465-72.

Seibenhener M L, Geetha T, Wooten M W. Sequestosome 1/p62-more than just a scaffold. *FEBS Lett.* 2007; 581, 175-9

Sonis S T. A Biological Approach to Mucositis. *J Supp Onc.* 2004; 2(1), 21-36.

Sonis. *Oral Diseases* in press & personal communication. 2010.

Sonis. *Current Opinions in Supportive and palliative care.* 2010; 4, 29-34.

Tosi M F. Innate immune responses to infection. *J Allergy Clin immunol.* 2005; 116, 241-9; quiz 50.

Tsuda, Y. and Okada, Y. Solution-Phase Peptide Synthesis, in Amino Acids, Peptides and Proteins in Organic Chemistry: Building Blocks, Catalysis and Coupling Chemistry, Volume 3 (ed A. B. Hughes) 2010, Wiley-VCH Verlag GmbH & Co. KGaA, Weinheim, Germany.

Williams J P, et al. Animal models for medical countermeasures to radiation exposure. Radiat Res, 2010. 173(4): 557-78.

Withers H R. Regeneration of intestinal mucosa after irradiation. Cancer. 1971; 28(1):75-81. Withers H R and Elkind M M. Radiosensitivity and fractionation response of crypt cells of mouse jejunum. Radiat Res. 1969; 38(3):598-613.

Wurthwein G, Rohdewald P. Activation of beclomethasone dipropionate by hydrolysis to beclomethasone-17-monopropionate. Biopharm Drug Dispos. 1990; 11:381-394.

Yu H B, Klelczewska A, Rozek A, Takenaka S, Li Y, Thorson L, et al. Sequestosome-1/p62 is the key intracellular target of innate defense regulator peptide. *J Biol Chem.* 2009; 284, 36007-11.

TABLE 1 all C-terminal amidated unless othe ise indicated****

| SEQ ID | Notes | 1 | 2 | 3 | 4 | 5 | 6 | 7 | 8 | 9 | 10 | 11 | 12 | 13 | 14 | 15 | ' | Length | Net charge |
|---|---|---|---|---|---|---|---|---|---|---|---|---|---|---|---|---|---|---|---|
| 1 | | | | | + | K | S | R | I | V | P | | | | | | | 6 | 3 |
| 2 | Ac denotes acetylation | | | Ac | K | S | R | I | V | P | | | | | | | | 6 | 2 |
| 3 | | | | | | + | S | R | I | V | P | A | | | | | | 6 | 2 |
| 4 | | | | | | + | S | R | I | V | P | | | | | | | 5 | 2 |
| 5 | | | | | | | + | R | I | V | P | A | | | | | | 5 | 2 |
| 6 | | | | | | | + | K | I | V | P | A | | | | | | 5 | 2 |
| 7 | *denotes D-amino acid | | | | | | + | R | I | V | P | A* | | | | | | 5 | 2 |

TABLE 1-continued all C-terminal amidated unless otherwise indicated****

| SEQ ID | Notes | 1 | 2 | 3 | 4 | 5 | 6 | 7 | 8 | 9 | 10 | 11 | 12 | 13 | 14 | 15 | ' | Length | Net charge |
|---|---|---|---|---|---|---|---|---|---|---|---|---|---|---|---|---|---|---|---|
| 8 | | | | | | + | R | | V | P | A | | | | | | | 4 | 2 |
| 9 | | | | | | + | R | I | | P | A | | | | | | | 4 | 2 |
| 10 | Free acid | | | | | + | R | I | V | P | A | OH | | | | | | 5 | 1 |
| 11 | | | | | | + | R | A | V | P | A | | | | | | | 5 | 2 |
| 12 | | | | | + | R | R | I | V | P | A | | | | | | | 6 | 3 |
| 13 | | | | | | + | R | K | V | P | A | | | | | | | 5 | 3 |
| 14 | | | | | | + | R | I | V | P | K | | | | | | | 5 | 3 |
| 15 | | | | | | + | R | P | V | P | A | | | | | | | 5 | 2 |
| 16 | | | | | | + | R | P | P | P | A | | | | | | | 5 | 2 |
| 17 | | | | | | + | R | I | V | P | P | | | | | | | 5 | 2 |
| 18 | | | | | | + | R | I | V | P | G | G | A | | | | | 7 | 2 |
| 19 | | | | | + | G | G | I | V | P | A | | | | | | | 6 | 1 |
| 20 | | | | | | + | G | | I | V | P | A | | | | | | 5 | 1 |
| 21 | | | | | | + | R | G | V | P | A | | | | | | | 5 | 2 |
| 22 | | | | | | + | R | I | V | P | G | | | | | | | 5 | 2 |
| 23 | | | | | | + | R | I | V | P | S | | | | | | | 5 | 2 |
| 24 | | | | | | + | R | I | V | P | L | | | | | | | 5 | 2 |
| 25 | | | | | | + | R | H | V | P | A | | | | | | | 5 | 2? |
| 26 | | | | | | | + | R | I | P | V | A | | | | | | 5 | 2 |
| 27 | | | | | | + | R | V | I | P | A | | | | | | | 5 | 2 |
| 28 | | | | | | + | R | I | I | P | A | | | | | | | 5 | 2 |
| 29 | | | | | | | + | A | V | P | I | R | | | | | | 5 | 2 |
| 30 | | | | | | | + | A | P | V | I | R | | | | | | 5 | 2 |
| 31 | cyclic head-to-tail | | | | | | -R | I | V | P | A- | | | | | | | 5 | 1 |
| 32 | cyclic-cystine link | | | | | -C | R | I | V | P | A | C- | | | | | | 7 | 1 |
| 33 | x denotes N-methyl in backbone | | | | | + | R | Ix | V | P | A | | | | | | | 5 | 2 |
| 34 | x denotes N-methyl in backbone | | | | | + | R | I | V | P | Ax | | | | | | | 5 | 2 |
| 35 | | | | | | + | R | I | V | P | F | | | | | | | 2 | 2 |
| 36 | | | | | | + | Cit | I | V | P | A | | | | | | | 5 | 1 |
| 37 | | | | | | + | R | L | V | P | A | | | | | | | 5 | 2 |
| 38 | | | | | | + | H | I | V | P | A | | | | | | | 5 | 1? |
| 39 | | | | | + | I | R | R | V | P | A | | | | | | | 6 | 3 |
| 40 | | | | | | + | A | R | V | P | A | | | | | | | 5 | 2 |
| 41 | | | | | | + | I | R | V | P | A | | | | | | | 5 | 2 |
| 42 | | | | | | + | O | I | V | P | A | | | | | | | 5 | 2 |

TABLE 1-continued all C-terminal amidated unless otherwise indicated****

| SEQ ID | Notes | 1 | 2 | 3 | 4 | 5 | 6 | 7 | 8 | 9 | 10 | 11 | 12 | 13 | 14 | 15 | ' | Length | Net charge |
|---|---|---|---|---|---|---|---|---|---|---|---|---|---|---|---|---|---|---|---|
| 43 | | | | | | + | S | I | V | P | A | | | | | | | 5 | 1 |
| 44 | | | | | + | V | S | I | I | K | P | A | R | V | P | S | L L | 13 | 3 |
| 45 | | | | | + | K | P | A | R | V | P | S | | | | | | 7 | 3 |
| 46 | | | | | + | R | | | V | P | S | L | L | | | | | 6 | 2 |
| 47 | | | | | + | K | P | R | A | V | P | | | | | | | 6 | 3 |
| 48 | | | | | + | P | A | R | V | P | | | | | | | | 5 | 2 |
| 49 | | | | | | + | I | R | V | P | | | | | | | | 4 | 2 |
| 50 | | | | | | + | R | | V | P | S | | | | | | | 8 | 2 |
| 51 | | | | | | + | R | | V | P | | | | | | | | 3 | 2 |
| 52 | | | | | | | | | + | P | S | V | P | G | S | | | 6 | 1 |
| 53 | | | | | | + | G | L | K | H | P | S | | | | | | 6 | 2? |
| 54 | | | | | | + | R | I | V | P | A | I | P | V | S | L | L | 11 | 2 |
| 55 | See Note 1 | | | | | | | | X₁ | X₂ | | P | | | | | | 3 | |
| 56 | See Note 2 | | | | | | | X₁ | X₂ | X₃ | P | | | | | | | 4 | |
| 57 | See Note 3 | | | | | | a | X₁ | X₂ | X₃ | P | | | | | | | 5 | |
| 58 | See Note 4 | | | | | | | X₁ | X₂ | X₃ | P | b | | | | | | 5 | |
| 59 | See Note 5 | | | | | a₁ | a₂ | X₁ | X₂ | X₃ | P | | | | | | | 6 | |
| 60 | See Note 6 | | | | | | a | X₁ | X₂ | X₃ | P | b | | | | | | 6 | |
| 61 | | | | | | | + | R | I | V | P | A | C | | | | | 6 | 2 |
| 62 | | | | | | | + | r | r | V | P | | | | | | | 4 | 3 |
| 63 | hydroxamic acid | | | | | | + | R | I | V | P | A | HOH | | | | | 5 | 2 |
| 64 | | | | | | | + | R | I | V | P | P | A | | | | | 6 | 2 |
| 65 | | | | | | | + | R | I | | P | A | | | | | | 5 | 2 |
| 66 | | | | | | | + | R | I | V | Pip | A | | | | | | 5 | 2 |
| 67 | | | | | | | + | R | I | V | Thz | A | | | | | | 5 | 2 |
| 68 | | | | | | | + | R | I | V | Fpro | | | | | | | 5 | 2 |
| 69 | | | | | | | + | R | I | V | Dhp | | | | | | | 5 | 2 |
| 70 | | | | | | | + | R | I | H | P | A | | | | | | 5 | 2 |
| 71 | | | | | | | + | R | I | W | P | A | | | | | | 5 | 2 |
| 72 | | | | | | | + | R | I | V | P | W | | | | | | 5 | 2 |
| 73 | | | | | | + | S | P | V | I | R | H | | | | | | 6 | 2 |
| 74 | | | | | | + | C | P | V | I | R | H | | | | | | 6 | 2 |
| 75 | | | | | | | | R | I | E | P | A | | | | | | 5 | 1 |
| 76 | | | | | | | + | R | I | V | P | E | | | | | | 5 | 1 |
| 77 | | | | | | | + | R | I | V | P | H | | | | | | 5 | 1 |
| 78 | | | | | | | + | R | S | V | P | A | | | | | | 5 | 1 |
| 79 | | | | | | | + | E | R | I | V | P | A | G | | | | 7 | 1 |
| 80 | | | | | | | + | K | V | I | P | S | | | | | | 5 | 2 |

TABLE 1-continued all C-terminal amidated unless otherwise indicated****

| SEQ ID | Notes | 1 | 2 | 3 | 4 | 5 | 6 | 7 | 8 | 9 | 10 | 11 | 12 | 13 | 14 | 15 | ' | Length | Net charge |
|---|---|---|---|---|---|---|---|---|---|---|---|---|---|---|---|---|---|---|---|
| 81 | | | | | | + | K | V | V | P | S | | | | | | | 5 | 2 |
| 82 | | | | | | | | + | K | P | R | P | | | | | | 4 | 3 |
| 83 | | | | | | + | R | | I | P | | | | | | | | 3 | 2 |
| 84 | | | | | | + | O | | V | P | | | | | | | | 3 | 2 |
| 85 | | | | | | + | S | | V | P | | | | | | | | 3 | 1 |
| 86 | | | | | | + | K | | V | P | | | | | | | | 3 | 2 |
| 87 | | | | | | + | R | | R | P | | | | | | | | 3 | 3 |
| 88 | | | | | | + | G | | V | P | | | | | | | | 3 | 1 |
| 88 | | | | | | | | + | K | H | P | | | | | | | 3 | 2 |
| 89 | | | | | | | R | | I | V | P | A | Y* | | | | | 6 | 2 |
| 90 | *denotes D-amino acid | | | | | | | | | | | | | | | | | | |
| 91 | R(tBg)V is linked via the side chain amino group of lysine to the valine of another R(tBg)V. | | | | | | R | tBg | V | K | R | tBg | V- | | | | | 8 | |
| 92 | mp2 = 4-Amino-1-methyl-1H-pyrrole-2-carboxylic acid | | | | | | R | | I | V | mp2 | A | NH₂ | | | | | 5 | |

****OH indicateds the free acid form of the peptide. Ac indicates acetylated. O indicated Omithine, Cit indicated Citruline, tBG = tert-butyl glycine, mp2 = 4-Amino-1-methyl-1H-pyrrole-2-carboxylic acid
x indicates NMe backbone (versus amide backbone).

What is claim is:

1. A method of reducing the incidence, severity and/or duration of oral mucositis in a subject who has been exposed to a damaging amount of radiation or chemotherapeutic agents, comprising administering to the patient an effective amount of:
   a) a peptide comprising an amino acid sequence of up to 7 amino acids, said peptide comprising the amino acid sequence of $X_1X_2X_3P$ (SEQ ID NO: 56), wherein:
   X1 is R;
   X2 is I or V, wherein X2 can be N-methylated;
   X3 is I or V, wherein X3 can be N-methylated;
   P is proline or a proline analogue;
   wherein SEQ ID NO: 56 is the first four amino acids at the N-terminus of the peptide, or a pharmaceutical salt, ester or amide thereof and a pharmaceutically-acceptable carrier, diluent, or excipient; or
   b) a peptide comprising the amino acid sequence of any of SEQ ID NOs: 5, 7, 10, 14, 17, 18, 22, 23, 24, 27, 28, 31, 34, 35, 63, 64, 66-69, 72, 76, 77, 90 and 92 or a pharmaceutical salt, ester or amide thereof and a pharmaceutically-acceptable carrier, diluent or excipient.

2. The method of claim 1, wherein the peptide is SEQ ID NO: 5 or a pharmaceutical salt, ester, or amide thereof and a pharmaceutically-acceptable carrier, diluent, or excipient.

3. The method of claim 1, wherein the peptide is administered orally, subcutaneously, intramuscularly, intravenously, transdermally, intranasally, by pulmonary administration, or by osmotic pump.

4. The method of claim 2, wherein the effective amount of peptide is at least 1.5 mg/kg.

5. The method of claim 2, wherein the peptide is administered to the patient every third day during radiation or chemotherapeutic agent administration.

6. A method of treating an individual suffering from a disease selected from the group consisting of mucositis and colitis or exposure to acute radiation comprising administering to the individual a peptide consisting of an amino acid sequence of SED ID Nos: 5, 7, 10, 14, 17, 18, 22, 23, 24, 27, 28, 31, 34, 35, 63, 64, 66-69, 72, 76, 77, 90, 91 and 92.

* * * * *

SEQUENCE LISTING

<160> NUMBER OF SEQ ID NOS: 92

<210> SEQ ID NO 1
<211> LENGTH: 6
<212> TYPE: PRT
<213> ORGANISM: Artificial Sequence
<220> FEATURE:
<223> OTHER INFORMATION: Immunological Peptide

<400> SEQUENCE: 1

Lys Ser Arg Ile Val Pro
1               5

<210> SEQ ID NO 2
<211> LENGTH: 6
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (1)..(1)
<223> OTHER INFORMATION: Xaa is equal to Acetylated K

<400> SEQUENCE: 2

Xaa Ser Arg Ile Val Pro
1               5

```
<210> SEQ ID NO 3
<211> LENGTH: 6
<212> TYPE: PRT
<213> ORGANISM: Artificial Sequence
<220> FEATURE:
<223> OTHER INFORMATION: IMMUNOLOGICAL PEPTIDE

<400> SEQUENCE: 3

Ser Arg Ile Val Pro Ala
1               5

<210> SEQ ID NO 4
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 4

Ser Arg Ile Val Ala
1               5

<210> SEQ ID NO 5
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 5

Arg Ile Val Pro Ala
1               5

<210> SEQ ID NO 6
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 6

Lys Ile Val Pro Ala
1               5

<210> SEQ ID NO 7
<211> LENGTH: 5
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (5)..(5)
<223> OTHER INFORMATION: Xaa is equal to D-Amino Acid of Ala

<400> SEQUENCE: 7

Arg Ile Val Pro Xaa
1               5

<210> SEQ ID NO 8
<211> LENGTH: 4
<212> TYPE: PRT
<213> ORGANISM: Artificial Sequence
<220> FEATURE:
<223> OTHER INFORMATION: IMMUNOLOGICAL PEPTIDE

<400> SEQUENCE: 8

Arg Val Pro Ala
```

```
<210> SEQ ID NO 9
<211> LENGTH: 4
<212> TYPE: PRT
<213> ORGANISM: Artificial Sequence
<220> FEATURE:
<223> OTHER INFORMATION: IMMUNOLOGICAL PEPTIDE

<400> SEQUENCE: 9

Arg Ile Pro Ala
1

<210> SEQ ID NO 10
<211> LENGTH: 5
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (5)..(5)
<223> OTHER INFORMATION: Xaa is equal to Ala-OH

<400> SEQUENCE: 10

Arg Ile Val Pro Xaa
1               5

<210> SEQ ID NO 11
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 11

Arg Ala Val Pro Ala
1               5

<210> SEQ ID NO 12
<211> LENGTH: 6
<212> TYPE: PRT
<213> ORGANISM: Artificial Sequence
<220> FEATURE:
<223> OTHER INFORMATION: IMMUNOLOGICAL PEPTIDE

<400> SEQUENCE: 12

Arg Arg Ile Val Pro Ala
1               5

<210> SEQ ID NO 13
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 13

Arg Lys Val Pro Ala
1               5

<210> SEQ ID NO 14
<211> LENGTH: 5
<212> TYPE: PRT
<213> ORGANISM: Artificial Sequence
<220> FEATURE:
<223> OTHER INFORMATION: IMMUNOLOGICAL PEPTIDE
```

```
<400> SEQUENCE: 14

Arg Ile Val Pro Lys
1               5

<210> SEQ ID NO 15
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 15

Arg Pro Val Pro Ala
1               5

<210> SEQ ID NO 16
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 16

Arg Ile Pro Pro Ala
1               5

<210> SEQ ID NO 17
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 17

Arg Ile Val Pro Pro
1               5

<210> SEQ ID NO 18
<211> LENGTH: 7
<212> TYPE: PRT
<213> ORGANISM: Artificial Sequence
<220> FEATURE:
<223> OTHER INFORMATION: IMMUNOLOGICAL PEPTIDE

<400> SEQUENCE: 18

Arg Ile Val Pro Gly Gly Ala
1               5

<210> SEQ ID NO 19
<211> LENGTH: 6
<212> TYPE: PRT
<213> ORGANISM: Artificial Sequence
<220> FEATURE:
<223> OTHER INFORMATION: IMMUNOLOGICAL PEPTIDE

<400> SEQUENCE: 19

Gly Gly Ile Val Pro Ala
1               5

<210> SEQ ID NO 20
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 20
```

```
Gly Ile Val Pro Ala
1               5

<210> SEQ ID NO 21
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 21

Ala Gly Val Pro Ala
1               5

<210> SEQ ID NO 22
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 22

Arg Ile Val Pro Gly
1               5

<210> SEQ ID NO 23
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 23

Arg Ile Val Pro Ser
1               5

<210> SEQ ID NO 24
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 24

Arg Ile Val Pro Leu
1               5

<210> SEQ ID NO 25
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 25

Arg His Val Pro Ala
1               5

<210> SEQ ID NO 26
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 26
```

Arg Ile Pro Val Ala
1               5

<210> SEQ ID NO 27
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 27

Arg Val Ile Pro Ala
1               5

<210> SEQ ID NO 28
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 28

Arg Ile Ile Pro Ala
1               5

<210> SEQ ID NO 29
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 29

Ala Val Pro Ile Arg
1               5

<210> SEQ ID NO 30
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 30

Ala Pro Val Ile Arg
1               5

<210> SEQ ID NO 31
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 31

Arg Ile Val Pro Ala
1               5

<210> SEQ ID NO 32
<211> LENGTH: 7
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (1)..(7)
<223> OTHER INFORMATION: cyclic peptide

```
<400> SEQUENCE: 32

Cys Arg Ile Val Pro Ala Cys
1               5

<210> SEQ ID NO 33
<211> LENGTH: 5
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (2)..(2)
<223> OTHER INFORMATION: Xaa is equal to I with an NMe backbone

<400> SEQUENCE: 33

Arg Xaa Val Pro Ala
1               5

<210> SEQ ID NO 34
<211> LENGTH: 5
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (5)..(5)
<223> OTHER INFORMATION: Xaa is equal to A with an N-methylated backbone

<400> SEQUENCE: 34

Arg Ile Val Pro Xaa
1               5

<210> SEQ ID NO 35
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 35

Arg Ile Val Pro Phe
1               5

<210> SEQ ID NO 36
<211> LENGTH: 5
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (1)..(1)
<223> OTHER INFORMATION: Xaa is equal to Citrulline

<400> SEQUENCE: 36

Xaa Ile Val Pro Ala
1               5

<210> SEQ ID NO 37
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 37
```

```
Arg Leu Val Pro Ala
1               5

<210> SEQ ID NO 38
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 38

His Ile Val Pro Ala
1               5

<210> SEQ ID NO 39
<211> LENGTH: 6
<212> TYPE: PRT
<213> ORGANISM: Artificial Sequence
<220> FEATURE:
<223> OTHER INFORMATION: IMMUNOLOGICAL PEPTIDE

<400> SEQUENCE: 39

Ile Arg Arg Val Pro Ala
1               5

<210> SEQ ID NO 40
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 40

Ala Arg Val Pro Ala
1               5

<210> SEQ ID NO 41
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 41

Ile Arg Val Pro Ala
1               5

<210> SEQ ID NO 42
<211> LENGTH: 5
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (1)..(1)
<223> OTHER INFORMATION: Xaa is equal to Ornithine

<400> SEQUENCE: 42

Xaa Ile Val Pro Ala
1               5

<210> SEQ ID NO 43
<211> LENGTH: 5
<212> TYPE: PRT
<213> ORGANISM: Artificial Sequence
<220> FEATURE:
```

```
<223> OTHER INFORMATION: IMMUNOLOGICAL PEPTIDE

<400> SEQUENCE: 43

Ser Ile Val Pro Ala
1               5

<210> SEQ ID NO 44
<211> LENGTH: 13
<212> TYPE: PRT
<213> ORGANISM: Artificial Sequence
<220> FEATURE:
<223> OTHER INFORMATION: IMMUNOLOGICAL PEPTIDE

<400> SEQUENCE: 44

Val Ser Ile Ile Lys Pro Ala Arg Val Pro Ser Leu Leu
1               5                   10

<210> SEQ ID NO 45
<211> LENGTH: 7
<212> TYPE: PRT
<213> ORGANISM: Artificial Sequence
<220> FEATURE:
<223> OTHER INFORMATION: IMMUNOLOGICAL PEPTIDE

<400> SEQUENCE: 45

Lys Pro Ala Arg Val Pro Ser
1               5

<210> SEQ ID NO 46
<211> LENGTH: 6
<212> TYPE: PRT
<213> ORGANISM: Artificial Sequence
<220> FEATURE:
<223> OTHER INFORMATION: IMMUNOLOGICAL PEPTIDE

<400> SEQUENCE: 46

Arg Val Pro Ser Leu Leu
1               5

<210> SEQ ID NO 47
<211> LENGTH: 6
<212> TYPE: PRT
<213> ORGANISM: Artificial Sequence
<220> FEATURE:
<223> OTHER INFORMATION: IMMUNOLOGICAL PEPTIDE

<400> SEQUENCE: 47

Lys Pro Arg Ala Val Pro
1               5

<210> SEQ ID NO 48
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 48

Pro Ala Arg Val Pro
1               5

<210> SEQ ID NO 49
<211> LENGTH: 4
<212> TYPE: PRT
<213> ORGANISM: Artificial Sequence
<220> FEATURE:
<223> OTHER INFORMATION: IMMUNOLOGICAL PEPTIDE
```

<400> SEQUENCE: 49

Ile Arg Val Pro
1

<210> SEQ ID NO 50
<211> LENGTH: 4
<212> TYPE: PRT
<213> ORGANISM: Artificial Sequence
<220> FEATURE:
<223> OTHER INFORMATION: IMMUNOLOGICAL PEPTIDE

<400> SEQUENCE: 50

Arg Val Pro Ser
1

<210> SEQ ID NO 51
<211> LENGTH: 3
<212> TYPE: PRT
<213> ORGANISM: Artificial Sequence
<220> FEATURE:
<223> OTHER INFORMATION: IMMUNOLOGICAL PEPTIDE

<400> SEQUENCE: 51

Arg Val Pro
1

<210> SEQ ID NO 52
<211> LENGTH: 6
<212> TYPE: PRT
<213> ORGANISM: Artificial Sequence
<220> FEATURE:
<223> OTHER INFORMATION: IMMUNOLOGICAL PEPTIDE

<400> SEQUENCE: 52

Pro Ser Val Pro Gly Ser
1               5

<210> SEQ ID NO 53
<211> LENGTH: 6
<212> TYPE: PRT
<213> ORGANISM: Artificial Sequence
<220> FEATURE:
<223> OTHER INFORMATION: IMMUNOLOGICAL PEPTIDE

<400> SEQUENCE: 53

Gly Leu Lys His Pro Ser
1               5

<210> SEQ ID NO 54
<211> LENGTH: 11
<212> TYPE: PRT
<213> ORGANISM: Artificial Sequence
<220> FEATURE:
<223> OTHER INFORMATION: IMMUNOLOGICAL PEPTIDE

<400> SEQUENCE: 54

Arg Ile Val Pro Ala Ile Pro Val Ser Leu Leu
1               5                   10

<210> SEQ ID NO 55
<211> LENGTH: 3
<212> TYPE: PRT
<213> ORGANISM: Artificial Sequence
<220> FEATURE:
<223> OTHER INFORMATION: IMMUNOLOGICAL PEPTIDE
<220> FEATURE:

```
<221> NAME/KEY: MISC_FEATURE
<222> LOCATION: (1)..(1)
<223> OTHER INFORMATION: Xaa is selected from the group consisting of K,
      H, R, S, T, O, Cit, Hci, Dab, Dpr, or glycine based compounds with
      basic functional groups substituted on the N-terminal, hSer, Val
      (betaOH)
<220> FEATURE:
<221> NAME/KEY: MISC_FEATURE
<222> LOCATION: (2)..(2)
<223> OTHER INFORMATION: Xaa is selected from the group consisting of V,
      I, K, P, and H

<400> SEQUENCE: 55

Xaa Xaa Pro
1

<210> SEQ ID NO 56
<211> LENGTH: 4
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (1)..(1)
<223> OTHER INFORMATION: Xaa is selected from the group consisting of K,
      H, R, S, T, O, Cit, Hci, Dab, Dpr, or glycine based compounds with
      basic functional groups substituted on the N-terminal, hSer, Val
      (betaOH)
<220> FEATURE:
<221> NAME/KEY: MISC_FEATURE
<222> LOCATION: (2)..(2)
<223> OTHER INFORMATION: Xaa is selected from the group consisting of A,
      I, L, V, K, P, G, H, R, S, O, Dab, Dpr, Cit, Hci, Abu, Nva, Nle
      and where Xaa can be N-methylated
<220> FEATURE:
<221> NAME/KEY: MISC_FEATURE
<222> LOCATION: (3)..(3)
<223> OTHER INFORMATION: Xaa is selected from the group consisting of I,
      V, P

<400> SEQUENCE: 56

Xaa Xaa Xaa Pro
1

<210> SEQ ID NO 57
<211> LENGTH: 5
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (1)..(1)
<223> OTHER INFORMATION: Xaa is selected from the group consisting of S,
      P, I, R, C, T, L, V, A, G, K, H, R, O, C, M and F
<220> FEATURE:
<221> NAME/KEY: MISC_FEATURE
<222> LOCATION: (2)..(2)
<223> OTHER INFORMATION: Xaa is selected from the group consisting of K,
      H, R, S, T, O, Cit, Hci, Dab, Dpr, or glycine based compounds with
      basic functional groups substituted on the N-terminal, hSer, Val
      (betaOH)
<220> FEATURE:
<221> NAME/KEY: MISC_FEATURE
<222> LOCATION: (3)..(3)
<223> OTHER INFORMATION: Xaa is selected from the group consisting of A,
      I, L, V, K, P, G, H, R, S, O, Dab, Dpr, Cit, Hci, Abu, Nva, Nle
      and where Xaa can be N-methylated
<220> FEATURE:
<221> NAME/KEY: MISC_FEATURE
<222> LOCATION: (4)..(4)
<223> OTHER INFORMATION: Xaa is selected from the group consisting of I,
      V, P
```

```
<400> SEQUENCE: 57

Xaa Xaa Xaa Xaa Pro
1               5

<210> SEQ ID NO 58
<211> LENGTH: 5
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (1)..(1)
<223> OTHER INFORMATION: Xaa is selected from the group consisting of K,
      H, R, S, T, O, Cit, Hci, Dab, Dpr, or glycine based compounds with
      basic functional groups substituted on the N-terminal, hSer, Val
      (betaOH)
<220> FEATURE:
<221> NAME/KEY: MISC_FEATURE
<222> LOCATION: (2)..(2)
<223> OTHER INFORMATION: Xaa is selected from the group consisting of A,
      I, L, V, K, P, G, H, R, S, O, Dab, Dpr, Cit, Hci, Abu, Nva, Nle
      and where Xaa can be N-methylated
<220> FEATURE:
<221> NAME/KEY: MISC_FEATURE
<222> LOCATION: (3)..(3)
<223> OTHER INFORMATION: Xaa is selected from the group consisting of I,
      V, P
<220> FEATURE:
<221> NAME/KEY: MISC_FEATURE
<222> LOCATION: (5)..(5)
<223> OTHER INFORMATION: Xaa is selected from the group consisting of A,
      A*, G, S, L, F, K, C, I, V, T, Y, R, H, O, and M, wherein A*
      denotes D amino acid of A

<400> SEQUENCE: 58

Xaa Xaa Xaa Pro Xaa
1               5

<210> SEQ ID NO 59
<211> LENGTH: 6
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (1)..(1)
<223> OTHER INFORMATION: Xaa is selected from the group consisting of K,
      I, R, H, O, L, V, A, and G
<220> FEATURE:
<221> NAME/KEY: MISC_FEATURE
<222> LOCATION: (2)..(2)
<223> OTHER INFORMATION: Xaa is selected from the group consisting of S,
      P, R, T, H, K, O, L, V, A, G, S, I
<220> FEATURE:
<221> NAME/KEY: MISC_FEATURE
<222> LOCATION: (3)..(3)
<223> OTHER INFORMATION: Xaa is selected from the group consisting of K,
      H, R, S, T, O, Cit, Hci, Dab, Dpr, or glycine based compounds with
      basic functional groups substituted on the N-terminal, hSer, Val
      (betaOH)
<220> FEATURE:
<221> NAME/KEY: MISC_FEATURE
<222> LOCATION: (4)..(4)
<223> OTHER INFORMATION: Xaa is selected from the group consisting of A,
      I, L, V, K, P, G, H, R, S, O, Dab, Dpr, Cit, Hci, Abu, Nva, Nle
      and where Xaa can be N-methylated
<220> FEATURE:
<221> NAME/KEY: MISC_FEATURE
<222> LOCATION: (5)..(5)
<223> OTHER INFORMATION: Xaa is selected from the group consisting of I,
      V, P

<400> SEQUENCE: 59
```

```
Xaa Xaa Xaa Xaa Xaa Pro
1               5

<210> SEQ ID NO 60
<211> LENGTH: 6
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (1)..(1)
<223> OTHER INFORMATION: Xaa is selected from the group consisting of S,
      R, K, H, O, T, I, L, V, A, and G
<220> FEATURE:
<221> NAME/KEY: MISC_FEATURE
<222> LOCATION: (2)..(2)
<223> OTHER INFORMATION: Xaa is selected from the group consisting of K,
      H, R, S, T, O, Cit, Hci, Dab, Dpr, or glycine based compounds with
      basic functional groups substituted on the N-terminal, hSer, Val
      (betaOH)
<220> FEATURE:
<221> NAME/KEY: MISC_FEATURE
<222> LOCATION: (3)..(3)
<223> OTHER INFORMATION: Xaa is selected from the group consisting of A,
      I, L, V, K, P, G, H, R, S, O, Dab, Dpr, Cit, Hci, Abu, Nva, Nle
      and where Xaa can be N-methylated
<220> FEATURE:
<221> NAME/KEY: MISC_FEATURE
<222> LOCATION: (4)..(4)
<223> OTHER INFORMATION: Xaa is selected from the group consisting of I,
      V, P
<220> FEATURE:
<221> NAME/KEY: MISC_FEATURE
<222> LOCATION: (6)..(6)
<223> OTHER INFORMATION: Xaa is selected from the group consisting of A,
      V, I, L, G, K, H, R, O, S, T, and F

<400> SEQUENCE: 60

Xaa Xaa Xaa Xaa Pro Xaa
1               5

<210> SEQ ID NO 61
<211> LENGTH: 6
<212> TYPE: PRT
<213> ORGANISM: Artificial Sequence
<220> FEATURE:
<223> OTHER INFORMATION: IMMUNOLOGICAL PEPTIDE

<400> SEQUENCE: 61

Arg Ile Val Pro Ala Cys
1               5

<210> SEQ ID NO 62
<211> LENGTH: 4
<212> TYPE: PRT
<213> ORGANISM: Artificial Sequence
<220> FEATURE:
<223> OTHER INFORMATION: IMMUNOLOGICAL PEPTIDE

<400> SEQUENCE: 62

Arg Arg Val Pro
1

<210> SEQ ID NO 63
<211> LENGTH: 5
<212> TYPE: PRT
<213> ORGANISM: Artificial Sequence
<220> FEATURE:
<223> OTHER INFORMATION: IMMUNOLOGICAL PEPTIDE
<220> FEATURE:
```

```
<221> NAME/KEY: MISC_FEATURE
<222> LOCATION: (5)..(5)
<223> OTHER INFORMATION: Xaa is equal to A-NHOH

<400> SEQUENCE: 63

Arg Ile Val Pro Xaa
1               5

<210> SEQ ID NO 64
<211> LENGTH: 6
<212> TYPE: PRT
<213> ORGANISM: Artificial Sequence
<220> FEATURE:
<223> OTHER INFORMATION: IMMUNOLOGICAL PEPTIDE

<400> SEQUENCE: 64

Arg Ile Val Pro Pro Ala
1               5

<210> SEQ ID NO 65
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 65

Arg Ile Gly Pro Ala
1               5

<210> SEQ ID NO 66
<211> LENGTH: 5
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (4)..(4)
<223> OTHER INFORMATION: Xaa is equal to Pip

<400> SEQUENCE: 66

Arg Ile Val Xaa Ala
1               5

<210> SEQ ID NO 67
<211> LENGTH: 5
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (4)..(4)
<223> OTHER INFORMATION: Xaa is equal to Thz

<400> SEQUENCE: 67

Arg Ile Val Xaa Ala
1               5

<210> SEQ ID NO 68
<211> LENGTH: 5
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (4)..(4)
```

```
<223> OTHER INFORMATION: Xaa is equal to Fpro

<400> SEQUENCE: 68

Arg Ile Val Xaa Ala
1               5

<210> SEQ ID NO 69
<211> LENGTH: 5
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (4)..(4)
<223> OTHER INFORMATION: Xaa is equal to Dhp

<400> SEQUENCE: 69

Arg Ile Val Xaa Ala
1               5

<210> SEQ ID NO 70
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 70

Arg Ile His Pro Ala
1               5

<210> SEQ ID NO 71
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 71

Arg Ile Trp Pro Ala
1               5

<210> SEQ ID NO 72
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 72

Arg Ile Val Pro Trp
1               5

<210> SEQ ID NO 73
<211> LENGTH: 6
<212> TYPE: PRT
<213> ORGANISM: Artificial Sequence
<220> FEATURE:
<223> OTHER INFORMATION: IMMUNOLOGICAL PEPTIDE

<400> SEQUENCE: 73

Ser Pro Val Ile Arg His
1               5

<210> SEQ ID NO 74
<211> LENGTH: 6
```

```
<212> TYPE: PRT
<213> ORGANISM: Artificial Sequence
<220> FEATURE:
<223> OTHER INFORMATION: IMMUNOLOGICAL PEPTIDE

<400> SEQUENCE: 74

Cys Pro Val Ile Arg His
1               5

<210> SEQ ID NO 75
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 75

Arg Ile Glu Pro Ala
1               5

<210> SEQ ID NO 76
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 76

Arg Ile Val Pro Glu
1               5

<210> SEQ ID NO 77
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 77

Arg Ile Val Pro His
1               5

<210> SEQ ID NO 78
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 78

Arg Ser Val Pro Ala
1               5

<210> SEQ ID NO 79
<211> LENGTH: 7
<212> TYPE: PRT
<213> ORGANISM: Artificial Sequence
<220> FEATURE:
<223> OTHER INFORMATION: IMMUNOLOGICAL PEPTIDE

<400> SEQUENCE: 79

Glu Arg Ile Val Pro Ala Gly
1               5

<210> SEQ ID NO 80
<211> LENGTH: 5
<212> TYPE: PRT
```

```
<213> ORGANISM: Artificial Sequence
<220> FEATURE:
<223> OTHER INFORMATION: IMMUNOLOGICAL PEPTIDE

<400> SEQUENCE: 80

Lys Val Ile Pro Ser
1               5

<210> SEQ ID NO 81
<211> LENGTH: 5
<212> TYPE: PRT
<213> ORGANISM: Artificial Sequence
<220> FEATURE:
<223> OTHER INFORMATION: IMMUNOLOGICAL PEPTIDE

<400> SEQUENCE: 81

Lys Val Val Pro Ser
1               5

<210> SEQ ID NO 82
<211> LENGTH: 4
<212> TYPE: PRT
<213> ORGANISM: Artificial Sequence
<220> FEATURE:
<223> OTHER INFORMATION: IMMUNOLOGICAL PEPTIDE

<400> SEQUENCE: 82

Lys Pro Arg Ser
1

<210> SEQ ID NO 83
<211> LENGTH: 3
<212> TYPE: PRT
<213> ORGANISM: Artificial Sequence
<220> FEATURE:
<223> OTHER INFORMATION: IMMUNOLOGICAL PEPTIDE

<400> SEQUENCE: 83

Arg Ile Pro
1

<210> SEQ ID NO 84
<211> LENGTH: 3
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (1)..(1)
<223> OTHER INFORMATION: Xaa is equal to Orn

<400> SEQUENCE: 84

Xaa Val Pro
1

<210> SEQ ID NO 85
<211> LENGTH: 3
<212> TYPE: PRT
<213> ORGANISM: Artificial Sequence
<220> FEATURE:
<223> OTHER INFORMATION: IMMUNOLOGICAL PEPTIDE

<400> SEQUENCE: 85

Ser Val Pro
1
```

```
<210> SEQ ID NO 86
<211> LENGTH: 3
<212> TYPE: PRT
<213> ORGANISM: Artificial Sequence
<220> FEATURE:
<223> OTHER INFORMATION: IMMUNOLOGICAL PEPTIDE

<400> SEQUENCE: 86

Lys Val Pro
1

<210> SEQ ID NO 87
<211> LENGTH: 3
<212> TYPE: PRT
<213> ORGANISM: Artificial Sequence
<220> FEATURE:
<223> OTHER INFORMATION: IMMUNOLOGICAL PEPTIDE

<400> SEQUENCE: 87

Arg Arg Pro
1

<210> SEQ ID NO 88
<211> LENGTH: 3
<212> TYPE: PRT
<213> ORGANISM: Artificial Sequence
<220> FEATURE:
<223> OTHER INFORMATION: IMMUNOLOGICAL PEPTIDE

<400> SEQUENCE: 88

Gly Val Pro
1

<210> SEQ ID NO 89
<211> LENGTH: 3
<212> TYPE: PRT
<213> ORGANISM: Artificial Sequence
<220> FEATURE:
<223> OTHER INFORMATION: IMMUNOLOGICAL PEPTIDE

<400> SEQUENCE: 89

Lys His Pro
1

<210> SEQ ID NO 90
<211> LENGTH: 6
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (6)..(6)
<223> OTHER INFORMATION: Xaa is equal to D-amino acid Tyr

<400> SEQUENCE: 90

Arg Ile Val Pro Ala Xaa
1               5

<210> SEQ ID NO 91
<211> LENGTH: 7
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (2)..(2)
<223> OTHER INFORMATION: Xaa is equal to tBG, tert-butyl glycine
```

```
<220> FEATURE:
<221> NAME/KEY: MISC_FEATURE
<222> LOCATION: (6)..(6)
<223> OTHER INFORMATION: Xaa is equal to tBG, tert-butyl glycine

<400> SEQUENCE: 91

Arg Xaa Val Lys Arg Xaa Val
1               5

<210> SEQ ID NO 92
<211> LENGTH: 6
<212> TYPE: PRT
<213> ORGANISM: Artificial Sequence
<220> FEATURE:
<223> OTHER INFORMATION: IMMUNOLOGICAL PEPTIDE
<220> FEATURE:
<221> NAME/KEY: MISC_FEATURE
<222> LOCATION: (4)..(4)
<223> OTHER INFORMATION: Xaa is equal to mp2, 4-Amino-1-methyl-1H-
      pyrrole-2-carboxylic acid
<220> FEATURE:
<221> NAME/KEY: MISC_FEATURE
<222> LOCATION: (6)..(6)
<223> OTHER INFORMATION: Xaa is equal to NH2

<400> SEQUENCE: 92

Arg Ile Val Xaa Ala Xaa
1               5
```